United States Patent
Polyak et al.

(10) Patent No.: US 6,432,640 B1
(45) Date of Patent: *Aug. 13, 2002

(54) P53-INDUCED APOPTOSIS

(75) Inventors: Kornelia Polyak, Brookline, MA (US); Bert Vogelstein, Baltimore; Kenneth W. Kinzler, BelAir, both of MD (US)

(73) Assignee: The Johns Hopkins University, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,750

(22) Filed: Sep. 17, 1998

Related U.S. Application Data

(60) Provisional application No. 60/059,153, filed on Sep. 17, 1997, and provisional application No. 60/079,817, filed on Mar. 30, 1998.

(51) Int. Cl.$^7$ .............................. C12Q 1/68; C07H 21/04
(52) U.S. Cl. ........................... 435/6; 536/23.1; 536/24.3
(58) Field of Search .................... 435/6, 91.1; 536/23.1, 536/24.3

(56) References Cited

FOREIGN PATENT DOCUMENTS

| EP | 0 390 323 A | 10/1990 |
|----|-------------|---------|
| EP | 0 761 822 A | 3/1997 |
| WO | 94/00601 A | 1/1994 |

OTHER PUBLICATIONS

Sequence search results from Genbank for SEQ ID No. 17, Jan. 1995.*
Human Receptor tyrosine kinase ddr gene, complete cds, accession U48705, Dec. 1996.*
Sakuma et al., FEBS Letters, vol. 398, pp 165–169, Dec. 1996.*
Vogelstein et al., Trends in Genetics, vol. 9, pp 138–141, 1993.*
Accession No. W08739, Sep. 1996.*
accession No. Z41916, Nov. 1994.*
Accession No. L30676, Dec. 1994.*
Accession No. A29425, Aug. 1996.*
accession No. X70987, Feb. 1994.*
accession No. A14852, 1993.*
Accession No. H53832, Sep. 1995.*
Database EMBL embl heidelberg Ac:x51439, Apr. 19, 1990 XP002089303.
Database EMBL embl heidelberg Ac:U33271, Sep. 19, 1995 XP002089304.
Database EMBL embl heidelberg AC:H42923, Nov. 17, 1995 XP002089305.
Polyak K. et al. "A Model for p53–induced apoptosis" Nature, vol. 389, Sep. 18, 1997, pp. 300–305.

* cited by examiner

*Primary Examiner*—W. Gary Jones
*Assistant Examiner*—Jehanne Souaya
(74) *Attorney, Agent, or Firm*—Banner & Witcoff, Ltd.

(57) ABSTRACT

The most well-documented biochemical property of p53 is its ability to transcriptionally activate genes. Many of the genes which are activated by p53 expression prior to the onset of apoptosis are predicted to encode proteins which could generate or respond to oxidative stress, including one that is implicated in apoptosis within plant meristems. p53 may result in apoptosis through a three-step process: (I) the transcriptional induction of specific redox-related genes; (ii) the formation of reactive oxygen species (ROS); and (iii) the oxidative degradation of mitochondrial components, rapidly leading to cell death. Transcription of other genes is decreased by p53. Examination of the level of transcription of p53-induced or repressed genes can be used to determine p53 status, to diagnose cancer, and to evaluate cytotoxicity or carcinogenicity of a test agent.

4 Claims, 9 Drawing Sheets

FIG. 3A

```
human PIG12  mpahslVMSSPALPAFLLCSTLLVIKMYVAIITGQVRLRKKAFANPEDALRHGGGp---QYCRSDPDVERCLRARNDMETIY
rat micGST   madlkqLMDNEVLMAFTSYATIILAKMMFLSSATAFQRLTNKVFANPEDCAGFGKGenakKFLRTDEKVERVRRALNDLENIV human PIG12  PFLFLGFVYSFLGPNPFVAWMHFLVFLVGRVAHTVAYLGKLRAPIRSVTYTLAQLPCASMALQILweaarhl
rat micGST   PFLGIGLLYSLSGPDLSTALIHFRIFVGARIYHTIAYLTPLPQPNRGLAFFVGYGVTLSMAYRLLrsrlyl-
```

FIG. 3B

```
human PIG3   ml-AVHFDKPGGPENLYVKEVAKPSPGEGEVLLKVAASALNRADLMQRQGQYDPPpgASNILGLEASGHVAELGPGCQ
Vigna TED2   mvkAIRVHEQGGPQVLKWEDVEIGEPKEGEVRRNKAVGVNFIDVYFRKGVYKPS-FPFTPGMEAVGVVTAVGAGLT human PIG3   GHWKIGDTAMALLPGGGQAYVTVPEGLLTQAAAIPEAWLTAFQLLHLVGNVQAGDYVLIHAGLSGVGTAAIQLT
Vigna TED2   GRQVGDLVAYAGQPMGSYAEEQILPANKVVPSSIDPPIAASIMLKGMTTHFLVRRCFKVEPGHTILVHAAAGGVGSLLCQWA human PIG3   RMAGAIPLVTAGSQKKLQMAEKLGAAAGFNYKKEDFSEATLKFTKGAGVNLILDCIGGSYWEKNVNGLALDGRWVLYGLMGGG
Vigna TED2   NALGATVIGTVSNKEKAAQAKEDGCHHVIIMKEEDFVARVNEITSGNGVEVVYDSVGKDTFEGSLAGLKLRGYMVSFGQSSGS human PIG3   DINGPlfskllfkrgslitsllrsrdnkykqmlvnafteqilphfstegpqrllpvldriypvteiqeahstwrptrt--
Vigna TED2   PDPVPlsslaaksflftrpslmqyvvtrdelleaagelfanvasgvlkvrvmhtyplseaakahedlenrktsgsivlip
```

FIG. 3C

```
human PIG8    miwghfsllccvvdslggeemadsvktflqdlargikdsiwgictiskldarigqkreegrrrrassvlagrrpqsierkqeseprivs
C.elegans f37c12  mvkfqiiardfyhgfidsfkgitfvrrireeeakevkveppkpvertvlnmrrekggifkrppeppkkdsfikklwqiyamnigflv human PIG8    rifqccawnggvfwfslllfyrvfipvlqsvtariigdpslhgdvwswlgfflTsifsavWVLPLFVLSKVVNAIWFQDIADLAFEVS
C.elegans f37c12  lwqvclilglffsffdrtdlghnigy----------------ILIIPIFFASRIIQALWFSDISGACMRAL human PIG8    GRKPHPFPSVSKIIADMLFNLLLQALFLIQGMFVSLFPIHLVGQLVSLLPMSLLYSLYCFEMRWFNKGIEMHQRLSNIERNWPYYFG
C.elegans f37c12  KLPPPEVPFSSMLAGTLISALHQIFFLIQGMLSQYLPIPLITPVIVYLHMALLNSMYCFDYFFDGYNLSFLRRKDIFESHWPYFLG human PIG8    FGLPwlfsqqcsphilsvaasflssflyslsapmkqrplakhisssccayspwws-----------------------
C.elegans f37c12  FGTPhalacsissnmfvnsvifallfpffiitsypanwmrkyeeeipkiafcrisymftelvgkfvksitptnnptaarnnaqn
```

FIG. 3D

```
human PIG6    .IGYEDPINPTYEATNAMYHRCLDYVLEELKhna------KAKVMVASHNEDTVRFALRRMEELGLHPADHRVYFGQLLGMCDQISFPLG.
Drosophila    .IGYEDPVNPTFEATTDMYHRTLSECLRRIKlmkdcdddarKIGIMVASHNEDTVRFAIQOMKEIGISPEDKVICFGQLLGMCDYITFPLG.
```

SEQUENCE LISTING

<160> NUMBER OF SEQ ID NOS: 93

<210> SEQ ID NO 1
<211> LENGTH: 20
<212> TYPE: DNA
<213> ORGANISM: Homo sapiens
<220> FEATURE:

<400> SEQUENCE: 1
cagcttgccc acccatgctc                                           20

<210> SEQ ID NO 2
<211> LENGTH: 18
<212> TYPE: DNA
<213> ORGANISM: Homo sapiens

<400> SEQUENCE: 2
ggccaggagt aagtaact                                             18

<210> SEQ ID NO 3
<211> LENGTH: 18
<212> TYPE: DNA

```
<213> ORGANISM: Homo sapiens

<400> SEQUENCE: 3
gccctggtct gccgcgga                                                    18

<210> SEQ ID NO 4
<211> LENGTH: 10
<212> TYPE: DNA
<213> ORGANISM: Homo sapiens

<400> SEQUENCE: 4
cccgcctctt                                                             10

<210> SEQ ID NO 5
<211> LENGTH: 10
<212> TYPE: DNA
<213> ORGANISM: Homo sapiens

<400> SEQUENCE: 5
aatctgcgcc                                                             10

<210> SEQ ID NO 6
<211> LENGTH: 10
<212> TYPE: DNA
<213> ORGANISM: Homo sapiens

<400> SEQUENCE: 6
gtgaccacgg                                                             10

<210> SEQ ID NO 7
<211> LENGTH: 10
<212> TYPE: DNA
<213> ORGANISM: Homo sapiens

<400> SEQUENCE: 7
tttcctctca                                                             10

<210> SEQ ID NO 8
<211> LENGTH: 10
<212> TYPE: DNA
<213> ORGANISM: Homo sapiens

<400> SEQUENCE: 8
tgcctgcacc                                                             10

<210> SEQ ID NO 9
<211> LENGTH: 10
<212> TYPE: DNA
<213> ORGANISM: Homo sapiens

<400> SEQUENCE: 9
tcacccacac                                                             10

<210> SEQ ID NO 10
<211> LENGTH: 10
<212> TYPE: DNA
<213> ORGANISM: Homo sapiens

<400> SEQUENCE: 10
taaacctgct                                                             10

<210> SEQ ID NO 11
<211> LENGTH: 10
```

```
<212> TYPE: DNA
<213> ORGANISM: Homo sapiens

<400> SEQUENCE: 11
cccaagctag                                                          10

<210> SEQ ID NO 12
<211> LENGTH: 10
<212> TYPE: DNA
<213> ORGANISM: Homo sapiens

<400> SEQUENCE: 12
agcccgccgc                                                          10

<210> SEQ ID NO 13
<211> LENGTH: 10
<212> TYPE: DNA
<213> ORGANISM: Homo sapiens

<400> SEQUENCE: 13
gacatcaagt                                                          10

<210> SEQ ID NO 14
<211> LENGTH: 10
<212> TYPE: DNA
<213> ORGANISM: Homo sapiens

<400> SEQUENCE: 14
tgtcctggtt                                                          10

<210> SEQ ID NO 15
<211> LENGTH: 10
<212> TYPE: DNA
<213> ORGANISM: Homo sapiens

<400> SEQUENCE: 15
agctcactcc                                                          10

<210> SEQ ID NO 16
<211> LENGTH: 10
<212> TYPE: DNA
<213> ORGANISM: Homo sapiens

<400> SEQUENCE: 16
aggctgtcca                                                          10

<210> SEQ ID NO 17
<211> LENGTH: 10
<212> TYPE: DNA
<213> ORGANISM: Homo sapiens

<400> SEQUENCE: 17
tgagtccctg                                                          10

<210> SEQ ID NO 18
<211> LENGTH: 10
<212> TYPE: DNA
<213> ORGANISM: Homo sapiens

<400> SEQUENCE: 18
ccctcctccg                                                          10

<210> SEQ ID NO 19
```

```
<211> LENGTH: 10
<212> TYPE: DNA
<213> ORGANISM: Homo sapiens

<400> SEQUENCE: 19
gaggccaaca                                                                 10

<210> SEQ ID NO 20
<211> LENGTH: 10
<212> TYPE: DNA
<213> ORGANISM: Homo sapiens

<400> SEQUENCE: 20
tggggccgca                                                                 10

<210> SEQ ID NO 21
<211> LENGTH: 10
<212> TYPE: DNA
<213> ORGANISM: Homo sapiens

<400> SEQUENCE: 21
tccttggacc                                                                 10

<210> SEQ ID NO 22
<211> LENGTH: 10
<212> TYPE: DNA
<213> ORGANISM: Homo sapiens

<400> SEQUENCE: 22
ctgggcctga                                                                 10

<210> SEQ ID NO 23
<211> LENGTH: 11
<212> TYPE: DNA
<213> ORGANISM: Homo sapiens

<400> SEQUENCE: 23
agctggtttc c                                                               11

<210> SEQ ID NO 24
<211> LENGTH: 10
<212> TYPE: DNA
<213> ORGANISM: Homo sapiens

<400> SEQUENCE: 24
gaggtgccgg                                                                 10

<210> SEQ ID NO 25
<211> LENGTH: 10
<212> TYPE: DNA
<213> ORGANISM: Homo sapiens

<400> SEQUENCE: 25
acaacgtcca                                                                 10

<210> SEQ ID NO 26
<211> LENGTH: 10
<212> TYPE: DNA
<213> ORGANISM: Homo sapiens

<400> SEQUENCE: 26
gtgcggagga                                                                 10
```

-continued

```
<210> SEQ ID NO 27
<211> LENGTH: 10
<212> TYPE: DNA
<213> ORGANISM: Homo sapiens

<400> SEQUENCE: 27
cgtcccggag                                                              10

<210> SEQ ID NO 28
<211> LENGTH: 10
<212> TYPE: DNA
<213> ORGANISM: Homo sapiens

<400> SEQUENCE: 28
gtgctcattc                                                              10

<210> SEQ ID NO 29
<211> LENGTH: 10
<212> TYPE: DNA
<213> ORGANISM: Homo sapiens

<400> SEQUENCE: 29
gctgactcag                                                              10

<210> SEQ ID NO 30
<211> LENGTH: 10
<212> TYPE: DNA
<213> ORGANISM: Homo sapiens

<400> SEQUENCE: 30
agatgctgca                                                              10

<210> SEQ ID NO 31
<211> LENGTH: 10
<212> TYPE: DNA
<213> ORGANISM: Homo sapiens

<400> SEQUENCE: 31
ctcagacagt                                                              10

<210> SEQ ID NO 32
<211> LENGTH: 10
<212> TYPE: DNA
<213> ORGANISM: Homo sapiens

<400> SEQUENCE: 32
tccggccgcg                                                              10

<210> SEQ ID NO 33
<211> LENGTH: 10
<212> TYPE: DNA
<213> ORGANISM: Homo sapiens

<400> SEQUENCE: 33
agccactgca                                                              10

<210> SEQ ID NO 34
<211> LENGTH: 10
<212> TYPE: DNA
<213> ORGANISM: Homo sapiens

<400> SEQUENCE: 34
gcttttaagg                                                              10
```

```
<210> SEQ ID NO 35
<211> LENGTH: 10
<212> TYPE: DNA
<213> ORGANISM: Homo sapiens

<400> SEQUENCE: 35
gggccaataa                                                            10

<210> SEQ ID NO 36
<211> LENGTH: 10
<212> TYPE: DNA
<213> ORGANISM: Homo sapiens

<400> SEQUENCE: 36
aagggctctt                                                            10

<210> SEQ ID NO 37
<211> LENGTH: 10
<212> TYPE: DNA
<213> ORGANISM: Homo sapiens

<400> SEQUENCE: 37
gtaagtgtac                                                            10

<210> SEQ ID NO 38
<211> LENGTH: 10
<212> TYPE: DNA
<213> ORGANISM: Homo sapiens

<400> SEQUENCE: 38
tgtacctgta                                                            10

<210> SEQ ID NO 39
<211> LENGTH: 10
<212> TYPE: DNA
<213> ORGANISM: Homo sapiens

<400> SEQUENCE: 39
aacgacctcg                                                            10

<210> SEQ ID NO 40
<211> LENGTH: 10
<212> TYPE: DNA
<213> ORGANISM: Homo sapiens

<400> SEQUENCE: 40
agtttgttag                                                            10

<210> SEQ ID NO 41
<211> LENGTH: 10
<212> TYPE: DNA
<213> ORGANISM: Homo sapiens

<400> SEQUENCE: 41
gactcgccca                                                            10

<210> SEQ ID NO 42
<211> LENGTH: 10
<212> TYPE: DNA
<213> ORGANISM: Homo sapiens

<400> SEQUENCE: 42
gggccaataa                                                            10
```

```
<210> SEQ ID NO 43
<211> LENGTH: 10
<212> TYPE: DNA
<213> ORGANISM: Homo sapiens

<400> SEQUENCE: 43
gggtttttat                                                              10

<210> SEQ ID NO 44
<211> LENGTH: 10
<212> TYPE: DNA
<213> ORGANISM: Homo sapiens

<400> SEQUENCE: 44
agaaatacca                                                              10

<210> SEQ ID NO 45
<211> LENGTH: 10
<212> TYPE: DNA
<213> ORGANISM: Homo sapiens

<400> SEQUENCE: 45
taccatcaat                                                              10

<210> SEQ ID NO 46
<211> LENGTH: 10
<212> TYPE: DNA
<213> ORGANISM: Homo sapiens

<400> SEQUENCE: 46
ggattgtctg                                                              10

<210> SEQ ID NO 47
<211> LENGTH: 10
<212> TYPE: DNA
<213> ORGANISM: Homo sapiens

<400> SEQUENCE: 47
tactagtcct                                                              10

<210> SEQ ID NO 48
<211> LENGTH: 10
<212> TYPE: DNA
<213> ORGANISM: Homo sapiens

<400> SEQUENCE: 48
aatattgaga                                                              10

<210> SEQ ID NO 49
<211> LENGTH: 10
<212> TYPE: DNA
<213> ORGANISM: Homo sapiens

<400> SEQUENCE: 49
gagggagttt                                                              10

<210> SEQ ID NO 50
<211> LENGTH: 10
<212> TYPE: DNA
<213> ORGANISM: Homo sapiens

<400> SEQUENCE: 50
```
aagggcgcgg 10

<210> SEQ ID NO 51
<211> LENGTH: 10
<212> TYPE: DNA
<213> ORGANISM: Homo sapiens

<400> SEQUENCE: 51
ttcacaaagg 10

<210> SEQ ID NO 52
<211> LENGTH: 10
<212> TYPE: DNA
<213> ORGANISM: Homo sapiens

<400> SEQUENCE: 52
ctgcacttac 10

<210> SEQ ID NO 53
<211> LENGTH: 10
<212> TYPE: DNA
<213> ORGANISM: Homo sapiens

<400> SEQUENCE: 53
gatcccaact 10

<210> SEQ ID NO 54
<211> LENGTH: 10
<212> TYPE: DNA
<213> ORGANISM: Homo sapiens

<400> SEQUENCE: 54
gggaagcaga 10

<210> SEQ ID NO 55
<211> LENGTH: 10
<212> TYPE: DNA
<213> ORGANISM: Homo sapiens

<400> SEQUENCE: 55
gctttctcac 10

<210> SEQ ID NO 56
<211> LENGTH: 10
<212> TYPE: DNA
<213> ORGANISM: Homo sapiens

<400> SEQUENCE: 56
ttcattataa 10

<210> SEQ ID NO 57
<211> LENGTH: 10
<212> TYPE: DNA
<213> ORGANISM: Homo sapiens

<400> SEQUENCE: 57
taaggagctg 10

<210> SEQ ID NO 58
<211> LENGTH: 10
<212> TYPE: DNA
<213> ORGANISM: Homo sapiens

<400> SEQUENCE: 58

```
tgagggaata                                                           10

<210> SEQ ID NO 59
<211> LENGTH: 10
<212> TYPE: DNA
<213> ORGANISM: Homo sapiens

<400> SEQUENCE: 59
gggatggcag                                                           10

<210> SEQ ID NO 60
<211> LENGTH: 9
<212> TYPE: DNA
<213> ORGANISM: Homo sapiens

<400> SEQUENCE: 60 tcttctctg                                                             9

<210> SEQ ID NO 61
<211> LENGTH: 10
<212> TYPE: DNA
<213> ORGANISM: Homo sapiens

<400> SEQUENCE: 61
gcaccttatt                                                           10

<210> SEQ ID NO 62
<211> LENGTH: 10
<212> TYPE: DNA
<213> ORGANISM: Homo sapiens

<400> SEQUENCE: 62
actttaaact                                                           10

<210> SEQ ID NO 63
<211> LENGTH: 10
<212> TYPE: DNA
<213> ORGANISM: Homo sapiens

<400> SEQUENCE: 63
ccattccact                                                           10

<210> SEQ ID NO 64
<211> LENGTH: 10
<212> TYPE: DNA
<213> ORGANISM: Homo sapiens

<400> SEQUENCE: 64
tcaaatgcat                                                           10

<210> SEQ ID NO 65
<211> LENGTH: 10
<212> TYPE: DNA
<213> ORGANISM: Homo sapiens

<400> SEQUENCE: 65
gaaaaatggt                                                           10

<210> SEQ ID NO 66
<211> LENGTH: 10
<212> TYPE: DNA
<213> ORGANISM: Homo sapiens
```

```
<400> SEQUENCE: 66
actaacaccc                                                              10

<210> SEQ ID NO 67
<211> LENGTH: 10
<212> TYPE: DNA
<213> ORGANISM: Homo sapiens

<400> SEQUENCE: 67
ttggggtttc                                                              10

<210> SEQ ID NO 68
<211> LENGTH: 498
<212> TYPE: DNA
<213> ORGANISM: Homo sapiens

<400> SEQUENCE: 68
ttaaagcaaa gaattccccg gtcccagcca tgtccaacgt cccccacaag tcctcgctgc       60
ccgagggcat ccgccctggc acgtgctga gaattcgcgg cttggttcct cccaatgcca      120
gcaggttcca tgtaaacctg ctgtgcgggg aggagcaggg ctccgatgcc gccctgcatt      180
tcaaccccgg gctggacacg tcggaggtgg tcttcaacag caaggagcaa ggctcctggg      240
gccgcgagga gcgcgggccg ggcgttcctt tccagcgcgg gcagcccttc gaggtgctca      300
tcatcgcgtc agacgacggc ttcaaggccg tggttgggga cgcccagtac caccacttcc      360
gccaccgcct gccgctggcg cgcgtgcgcc tggtggaggt gggcggggac gtgcagctgg      420
actccgtgag gatcttctga gcagaagccc aggcggcccg gggccttggc tggcaaataa      480
agcgttagcc cgcagcgc                                                    498

<210> SEQ ID NO 69
<211> LENGTH: 993
<212> TYPE: DNA
<213> ORGANISM: Homo sapiens

<400> SEQUENCE: 69
cggcggcgcg cgatcgaggt cgggtcgccg tccagcctgc agcatgagcg cccccagcgc       60 gaccccatc ttcgcgcccg gcgagaactg cagccccgcg tgggggggcgg cgcccgcggc      120 ctacgacgca gcggacacgc acctgcgcat cctgggcaag ccggtgatgg agcgctggga      180
gaccccctat atgcacgcgc tggccgccgc cgcctcctcc aaaggggggcc gggtcctgga      240 ggtgggcttt ggcatggcca tcgcagcgtc aaaggtgcag gaggcgccca ttgatgagca      300
ttggatcatc gagtgcaatg acggcgtctt ccagcggctc cgggactggg ccccacggca      360
gacacacaag gtcatcccct tgaaaggcct gtgggaggat gtggcaccca ccctgcctga      420
cggtcacttt gatgggatcc tgtacgacac gtacccactc tcggaggaga cctggcacac      480
acaccagttc aacttcatca gaaccacgc ctttcgcctg ctgaagccgg ggggcgtcct      540
cacctactgc aacctcacct cctgggggga gctgatgaag tccaagtact cagacatcac      600
catcatgttt gaggagacgc aggtgcccgc gctgctggag gccggcttcc ggagggagaa      660
catccgtacg gaggtgatgg cgctggtccc accggccgac tgccgctact acgccttccc      720
acagatgatc acgcccctgg tgaccaaagg ctgagccccc accccggccc ggccacaccc      780
atgccctccg ccgtgccttc ctggccggga gtccagggtg tcgcaccagc cctgggctga      840
tcccagctgt gtgtcaccag aagctttccc ggcttctctg tgagggtcc caccagccca      900 gggctgatcc cagctgtgtg tcaccagcag ctttcccagc ttgctctgtg agggtcactg      960
```

```
ctgcccactg cagggtgccc tgaggtgaag ccg                                  993
```

<210> SEQ ID NO 70
<211> LENGTH: 1670
<212> TYPE: DNA
<213> ORGANISM: Homo sapiens

<400> SEQUENCE: 70

```
ccagccgtcc attccggtgg aggcagaggc agtcctgggg ctctggggct cggcttttgt     60
caccgggacc cgcagagcca gaaccactcg gcgccgctgt gcatgggag gggagccggg    120
ccaggagtaa gtaactcata cgggcgccgg ggacccgggt cggctggggg cttccaactc    180
agagggagtg tgatttgcct gatcctcttc ggcgttgtcc tgctctgccg catccagccc    240
tgtaccgcca tcccacttcc cgccgttccc atctgtgttc cgggtgggat cggtctggag    300
gcggccgagg acttcccagg caggagctcg ggcggaggc gggtccgcgg cagaccaggg    360
cagcgaggcg ctggccggca gggggcgctg cggtgccagc ctgaggctgg ctgctccgcg    420
aggatacagc ggcccctgcc ctgtcctgtc ctgccctgcc ctgtcctgtc ctgccctgcc    480
ctgccctgtc ctgtcctgcc ctgccctgcc ctgtgtcctc agacaatatg ttagccgtgc    540
actttgacaa gccggagga ccggaaaacc tctacgtgaa ggaggtggcc aagccgagcc    600
cggggagggg tgaagtcctc ctgaaggtgg cggccagcgc cctgaaccgg cggacttaa    660
tgcagagaca aggccagtat gacccacctc caggagccag caacattttg ggacttgagg    720
catctggaca tgtggcagag ctggggcctg gctgccaggg acactggaag atcggggaca    780
cagccatggc tctgctcccc ggtgggggcc aggctcagta cgtcactgtc cccgaagggc    840
tcctcatgcc tatcccagag ggattgaccc tgacccaggc tgcagccatc ccagaggcct    900
ggctcaccgc cttccagctg ttacatcttg tgggaaatgt tcaggctgga gactatgtgc    960
taatccatgc aggactgagt ggtgtgggca cagctgctat ccaactcacc cggatggctg   1020
gagctattcc tctggtcaca gctggctccc agaagaagct tcaaatggca gaaaagcttg   1080
gagcagctgc tggattcaat tacaaaaaag aggatttctc tgaagcaacg ctgaaattca   1140
ccaaaggtgc tggagttaat cttattctag actgcatagg cggatcctac tgggagaaga   1200
acgtcaactg cctggctctt gatggtcgat gggttctcta tggtctgatg ggaggaggtg   1260
acatcaatgg gcccctgttt tcaaagctac ttttaagcg aggaagtctg atcaccagtt   1320
tgctgaggtc tagggacaat aagtacaagc aaatgctggt gaatgctttc acggagcaaa   1380
ttctgcctca cttctccacg gagggccccc aacgtctgct gccggttctg acagaatct   1440
acccagtgac cgaaatccag gaggcccata gtacatggag gccaacaaga acataggcaa   1500
gatcgtcctg gaactgcccc agtgaaggag gatgggggca ggacaggacg cggccacccc   1560
aggccttcc agagcaaacc tggagaagat tcacaataga caggccaaga aacccggtgc   1620
ttcctccaga gccgtttaaa gctgatatga ggaaataaag agtgaactgg              1670
```

<210> SEQ ID NO 71
<211> LENGTH: 526
<212> TYPE: DNA
<213> ORGANISM: Homo sapiens

<400> SEQUENCE: 71

```
cagctacagc acagatcagc accatgaagc ttctcacggg cctggttttc tgctccttgg     60
tcctgagtgt cagcagccga agcttctttt cgttccttgg cgaggctttt gatgggctc    120
```

-continued

| | |
|---|---|
| gggacatgtg gagagcctac tctgacatga gagaagccaa ttacatcggc tcagacaaat | 180 |
| acttccatgc tcgggggaac tatgatgctg ccaaaagggg acctggggt gcctgggccg | 240 |
| cagaagtgat cagcaatgcc agagagaata tccagagact cacaggccat ggtgcggagg | 300 |
| actcgctggc cgatcaggct gccaataaat ggggcaggag tggcagagac cccaatcact | 360 |
| tccgacctgc tggcctgcct gagaaatact gagcttcctc ttcactctgc tctcaggaga | 420 |
| cctggctatg agccctcggg gcagggattc aaagttagtg aggtctatgt ccagagaagc | 480 |
| tgagatatgg catataatag gcatctaata aatgcttaag aggtgg | 526 |

<210> SEQ ID NO 72
<211> LENGTH: 842
<212> TYPE: DNA
<213> ORGANISM: Homo sapiens

<400> SEQUENCE: 72

| | |
|---|---|
| gcctcaaggg ctacgtcaac cacagcctgt ccgtcttcca caccaaggac ttccaggacc | 60 |
| ctgatgggat tgagggctca gaaaacgtga ctctgtgcag atacagggac taccgcaatc | 120 |
| ccccgattac aacttctccg agcagttctg gttcctcctg gccatccgcc tggccttcgt | 180 |
| catcctcttt gagcacgtgg ccttgtgcat caagctcatc gccgcctggt tcgtgcccga | 240 |
| catccctcag tcggtgaaga acaaggttct ggaggtgaag taccagaggc tgcgtgagaa | 300 |
| gatgtggatg aaggcagag ctggtggg gtgggggctg ctctcggcc cccaatgcct | 360 |
| gcccatccca ccccagcatc catcttcagt gccaggagca cagacgtgta gggccagagc | 420 |
| ccgtccagag gccaccagga gctgagacag tgccaccacc agcacctccc acaaacccac | 480 |
| cctgtgcgtg ttgaggggtg ctgtgagaag gctgtgccca tgtggggccg caggaatccc | 540 |
| ctgtatgttc agggctgtga gctgccaccc tattccgcct gctccgtctt tgtggggctc | 600 |
| tcaggcttgg cacagccctg acttgaactc tgggtgagcc tgggcaccca cagaactggg | 660 |
| agtgagggct cctcaggcag ccacaaggca ggaaaactgg cgcaaatttc ctgggcctcc | 720 |
| ctctgacttc tgggcgccag atcctgccgt gccccctacc tggctgttgg gggtgtcctg | 780 |
| agcccacctc gctggcctgt tcccttcagc caacccgttt ctgcagtaaa attaagcctg | 840 |
| tc | 842 |

<210> SEQ ID NO 73
<211> LENGTH: 901
<212> TYPE: DNA
<213> ORGANISM: Homo sapiens

<400> SEQUENCE: 73

| | |
|---|---|
| ggcgcatacc tggcccagga gcgagcccgt gcgcagatcg gctatgagga ccccatcaac | 60 |
| cccacgtacg aggccaccaa cgccatgtac cacaggtgcc tggactacgt gttggaggag | 120 |
| ctgaagcaca acgccaaggc caaggtgatg gtggcctccc acaatgagga cacagtgcgc | 180 |
| ttcgcactgc gcaggatgga ggagctgggc ctgcatcctg ctgaccacca ggtgtacttt | 240 |
| ggacagctgc taggcatgtg tgaccagatc agcttcccgc tgggccacgg ctggctaccc | 300 |
| cgtgtacaag tacgtgccct atggcccgt gatggaggtg ctgccctact tgtcccgcc | 360 |
| gtgccctgga agaacagcag cctcatgaag ggcacccatt cgggagcggc actggctgtg | 420 |
| gctggagctc ttgaagcggc tccgaactgg caacctcttc catcgccctg cctagcaccc | 480 |
| gccagcacac cctctagcct tccagcaccc ccgccccct gctccaggcc attcaaccaa | 540 |
| caagctgcaa gccaaacccc aatccttcaa cacagattca cctttttca ccccaccact | 600 |

-continued

```
ttgcagagct tgcttggagg tgaggtcagg tgcctcccag cccttgccca gagtatgggc      660
actcaggtgt gggccgaacc tgatacctgc ctgggacagc cactggaaac ttttgggaac      720
tctcctctga aatgtgtggg cccaaggccc ccacctctgt gacccccatg tccttggacc      780
tagaggattg tccaccttct gccaaggcca gcccacacag cccgagcccc ttggggagca      840
gtggccgggc tggggaggcc tgcctggtca ataaaccact gttcctgcaa aaaaaaaaa      900 a                                                                       901
```

<210> SEQ ID NO 74
<211> LENGTH: 1677
<212> TYPE: DNA
<213> ORGANISM: Homo sapiens

<400> SEQUENCE: 74

```
cacgcgcagc atagcagagt cgacactaga ggcatccaaa gaataccggc acgagcaggc       60
ggcgcgggcg gcggttaaaa tgtcggttcc aggaccttac caggcggcca ctgggccttc      120
ctccgcacca tccgcacctc catcctatga agagacagtg gctgttaaca gttattaccc      180
cactcctcca gctcccatgc ctgggccaac tacgggcttt gtgacggggc ctgatgggaa      240
gggcatgaat cctccttcgt attataccca gccagcgccc atccccaata acaatccaat      300
taccgtgcag acggtctacg tgcagcaccc catcaccttt ttggaccgcc ctatccaaat      360
gtgttgtcct tcctgcaaca agatgatcgt gagtcagctg tcctataacg ccggtgctct      420
gacctggctg tcctgcggga gcctgtgcct gctgggggtg catagcggcc tgctgcttca      480 tcccttctg cgtggatgcc ctgcaggacg tggaccatta ctgtcccaac tgcagagctc      540
tcctgggcac ctacaagcgt ttgtaggact cagccagacg tggagggagc cgggtgccgc      600
aggaagtcct ttccacctct catccagctt cacgcctggt ggaggttctg ccctggtggt      660
ctcacctctc caggggggccc accttcatgt cttcttttgg ggggaatacg tcgcaaaact      720
aacaaatctc caaaccccag aaattgctgc ttggagtcgt gcataggact tgcaaagaca      780
ttccccttga gtgtcagttc cacggtttcc tgcctccctg agaccctgag tcctgccatc      840
taactgttga tcattgccct atccgaatat tttcctgtcg accccgggcc accagtggct      900
cttttttcct gcttccatgg gcctttctgg tggcagtctc aaactgagga agccacagtt      960
gcctcatttt tgaggctgtt ctccccagga gcttcggctg gaaccaggcc tttaggtggc     1020
cttaccattt atctctatat ccggctcttt cccgttccct ggatggacaa aaatcttgcc     1080
cttgacagga ctttaacagg gcttgggctt tgagattctg ttaacccgca ggacttcatt     1140
aggcacacaa gattcacctt aatttctcta aatttttttt ttttttaaaat accaagggaa     1200 gggggctaat taacaaccca gtacaggaca tatccacaag ggtcggtaaa tggcatgcta     1260
ggaaaaatag gggccttgga tcttattcac tggccctgtc ttccccttgg tttctcttgt     1320
ggccagatct ttcagttgcc ccttttccat aacagggat ttttttttctt cataggagtt     1380 aattattatg ggaacagttt tttatggacc tccctttttgg tctggaaata cctttctcgaa     1440 cagaatttct ttttttttaaa aaaaaacaga gatgggtct tactatgttg cccaggctgg     1500
tgtcgaactc ctgggctcaa gcgatccttc tgccttggcc tcccgaagtg ctgggattgc     1560
aggcataagc ttaccatgct gggcctgaac ataatttcaa gaggaggatt tataaaacca     1620
ttttctgtaa tcaaatgatt ggtgtcattt tcccatttgc acaatgtagt ctcactt       1677
```

<210> SEQ ID NO 75

<211> LENGTH: 2608
<212> TYPE: DNA
<213> ORGANISM: Homo sapiens

<400> SEQUENCE: 75

| | | | | | |
|---|---|---|---|---|---|
| agctcgccgg | cctttggtct | ccaggacttg | tcccagcagc | ccctcgaact | gagaattaca | 60 |
| ccatcggacc | cctggctctg | aggccttcag | acttggactg | tgtcacactg | ccaggcttcc | 120 |
| agggctccaa | cttgcagacg | gcctgttgtg | ggacagtctc | tgtaatcgcg | aaagcaacca | 180 |
| tggaagacct | gggggaaaac | accatggttt | tatccaccct | gagatctttg | aacaacttca | 240 |
| tctctcagcg | tgtggaggga | ggctctggac | tggatatttc | tacctcggcc | ccaggttctc | 300 |
| tgcagatgca | gtaccagcag | agcatgcagc | tggaggaaag | agcagagcag | atccgttcga | 360 |
| agtcccacct | catccaggtg | gagcgggaga | aaatgcagat | ggagctgagt | cacaagaggg | 420 |
| ctcgagtgga | gctggagaga | gcagccagca | ccagtgccag | gaactacgag | cgtgaggtcg | 480 |
| accgcaacca | ggagctcctg | acgcgcatcc | ggcagcttca | ggagcgggag | gccggggcgg | 540 |
| aggagaagat | gcaggagcag | ctggagcgca | acaggcagtg | tcagcagaac | ttggatgctg | 600 |
| ccagcaagag | gctgcgtgag | aaagaggaca | gtctggccca | ggctggcgag | accatcaacg | 660 |
| cactgaaggg | gaggatctcg | gaactgcagt | ggagcgtgat | ggaccaggag | atgcgggtga | 720 |
| agcgcctgga | gtcggagaag | caggacgtgc | aggagcagct | ggacctgcaa | cacaaaaaat | 780 |
| gccaggaagc | caatcagaaa | atccaggaac | tccaggccag | ccaagaagca | agagcagacc | 840 |
| acgagcagca | gattaaggat | ctggagcaga | agctgtccct | gcaagagcag | gatgcagcga | 900 |
| ttgtgaagaa | catgaagtct | gagctggtac | ggctccctag | gctggaacgg | agctggagc | 960 |
| agctgcggga | ggagagcgca | ctgcgggaga | tgagagagac | caacgggctg | ctccaggaag | 1020 |
| agctggaagg | gctgcagagg | aagctggggc | gccaggagaa | gatgcaggag | acgctggttg | 1080 |
| gcttggagct | ggagaacgag | aggctgctgg | ccaagctgca | aagctgggag | agactggacc | 1140 |
| agaccatggg | cctgagcatc | aggactccag | aagacctttc | cagattcgtg | gttgagctgc | 1200 |
| agcagaggga | gcttgccttg | aaggacaaga | acagcgccgt | caccagcagc | gcccgggggc | 1260 |
| tggagaaggc | caggcagcag | ctgcaggagg | agctccggca | ggtcagcggc | cagctgttgg | 1320 |
| aggagaggaa | gaagcgcgag | acccacgagg | cgctggcccg | gaggctccag | aaacgggtcc | 1380 |
| tgctgctcac | caaggagcgg | gacggtatgc | gggccatcct | ggggtcctac | gacagcgagc | 1440 |
| tgaccccggc | cgagtactca | ccccagctga | cgcggcgcat | cgggaggct | gaggatatgg | 1500 |
| tgcagaaggt | gcacagccac | agcgccgaga | tggaggctca | gctgtcgcag | gccctggagg | 1560 |
| agctgggagg | ccagaaacaa | agagcagaca | tgctggagat | ggagctgaag | atgctgaagt | 1620 |
| ctcagtccag | ctctgccgaa | cagagcttcc | tgttctccag | ggaggaggcg | gacacgctca | 1680 |
| ggttgaaggt | cgaggagctg | gaaggcgagc | ggagtcggct | ggaggaggaa | aagaggatgc | 1740 |
| tggaggcaca | gctggagcgg | cgagctctgc | agggtgacta | tgaccagagc | aggaccaaag | 1800 |
| tgctgcacat | gagcctgaac | cccaccagtg | tggccaggca | cgcctgcgc | gaggaccaca | 1860 |
| gccagctgca | ggcggagtgc | gagcgactgc | gcgggctcct | gcgcgccatg | gagagaggag | 1920 |
| gcaccgtccc | agccgacctt | gaggctgccg | ccgcgagtct | gccatcgtcc | aaggaggtgg | 1980 |
| cagagctgaa | gaagcaggtg | gagagtgccg | agctgaagaa | ccagcggctc | aaggaggttt | 2040 |
| tccagaccaa | gatccaggag | ttccgcaagg | cctgctacac | gctcaccggc | taccagatcg | 2100 |
| acatcaccac | ggagaaccag | taccggctga | cctcgctgta | cgccgagcac | ccaggcgact | 2160 |
| gctcatcttc | aaggccacca | gcccctcggg | ttccaagatg | cagctactgg | agacagagtt | 2220 |

```
ctcacacacc gtgggcgagc tcatcgaggt gcacctgcgg cgccaggaca gcatccctgc    2280
cttcctcagc tcgctcaccc tcgagctctt cagccgccag accgtggcgt agcctgcagg    2340
ctcgggggca tagccggagc cactctgctt ggcctgacct gcaggtcccc tgccccgcca    2400
gccacaggct gggtgcacgt cctgcctctc agccccaca gggcagcagc atgactgaca    2460
gacacgctgg gacctacgtc gggcttcctg ctggggcggc cagcaccctc tccacgtgca    2520
gaccccatgc gtcccggagc ctggtgtgtg ggcgtcggcc accagcctgg gttcctcacc    2580
ttgtgaaata aaatcttctc ccctaaaa                                       2608
```

<210> SEQ ID NO 76
<211> LENGTH: 2326
<212> TYPE: DNA
<213> ORGANISM: Homo sapiens

<400> SEQUENCE: 76

```
aggccggaga ggaggcggtg cggcggtggc cgtgcggaga cccggtccag acgcctggcg     60
gccgccggca cacaaggcgc tttctagctc cctcccccga gcgcacagcc cgcctccttc    120
cgcggcgcct gcagtggcac ggattgctct gccctaccgt gacgcgctcc ggagacgctc    180
tgcgggtcct ggacaccggg tccggcgcg tggggacgac agacggaggc gaacgcatcc    240
ggtagccggt ccgcgagcca tcgttcgggg cgcagtcctc tccccggctg ccctcctttt    300
ctccggggca ttcgccaccg cttccctggg gctgagacga ccggttcgtc gcctccttgc    360
ccgtgaccgt cgctagaact cagttgtgcg ttgcggccag tcgccactgc tgagtggaag    420
caaaatgtca gtcagtgtgc atgagaaccg caagtccagg gccagcagcg gctccattaa    480
catctatctg tttcacaagt cctcctacgc tgacagcgtc ctcactcacc tgaatctttt    540
acgccagcag cgtctcttca ctgacgtcct tctccatgcc ggaaatagga ccttcccttg    600
ccaccgggca gtgctggctg catgcagtcg ctactttgag gccatgttca gtggtggcct    660
gaaagagagc caggacagtg aggtcaactt tgacaattcc atccacccag aagtcttgga    720
gctgctgctt gactatgcgt actcctcccg ggtcattcat caattggaag gaaaatgcag    780
aaattcgctc ctgggaagct tggtgacatg ctggagtttc aaggacatcc gggatgcatg    840
tgcagagttc ctgaaaaaga acctgcatcc caccaactgc ctgggcatgc tgctgctgtc    900
tgatgcacac cagtgcacca agctgtacga actatcttgg agaatgtgtc tcagcaactt    960
ccaaaccatc aggaagaatg aagatttcct ccagctgccc caggacatgg tagtgcaact   1020
cttgtccagt gaagagctgg agacagagga tgaaaggctt gtgtacgagt ctgcaattaa   1080
ctggatcagc tatgacctga agaagcgcta ttgctacctc ccagaactgt tgcagacagt   1140
aacgcgggca cttctgccag ccatctatct catggagaat gtggccatgg aggaactcat   1200
caccaagcag agaaagagta aggaaattgt ggaagaggcc atcaggtgca aactaaaaat   1260
cctgcagaat gacggtgtgg taaccagcct ctgtgcccga cctcggaaaa ctggccatgc   1320
cctcttcctt ctgggaggac agactttcat gtgtgacaag ttgtatctgg tagaccagaa   1380
ggccaaagaa atcattccca aggctgacat tcccagccca agaaaagagt ttagtgcatg   1440
tgcgattggc tgcaaagtgt acattactgg ggggcggggg tctgaaaatg gggtctcgaa   1500
agatgtctgg gtttatgata ccctgcacga ggagtggtcc aaggctgccc ccatgctggt   1560
ggccaggttt ggccatggct ctgctgaact gaagcactgc ctgtatgtgg ttgggggggca   1620 cacggccgca actggctgcc tccgggcctc cccctcagtc tctctaaagc aggtagaaca   1680
```

-continued

```
ttatgacccc acaatcaaca aatggaccat ggcggcccca cgtccgagaa ggcgttacaa      1740
ctgcgcacag gtagtgagtg ccaaacttaa gttatttgct ttcggaggta ccagtgtcag      1800
tcatgacaag ctccccaaag ttcagtgtta cgatcagtgt gaaaacaggt ggactgtacc      1860
ggccacctgt ccccagccct ggcgtataca cagccaagca agctgtcctg ggggaaccca      1920 ggattttta ttatgggggg tgatacagaa tttctctgcc tgcttctgct tataaattcg      1980
caacagtgag acttaccagt ggaccaaagg tgggagatgt gacagcaaag cgcatgagct      2040
gccatgctgt tggcctctgg aaacaaactc ttacgtggtt ggaggatact ttgggcattc      2100
agcgatgcaa gactttggac tgctacgatc caacattaga cgtgtggaac agcatcacca      2160
ctgtcccgta ctcgctgatt cctactgcat tttgtcagca cctggaaaca tctgccttct      2220
taaatgcagt acattctaaa gagaagatga gcatgagctc actccatcac tcgatgagat      2280
aatatgagat ttctacttcg gagaggccaa gtctaatgaa gagaaa                    2326
```

<210> SEQ ID NO 77
<211> LENGTH: 2302
<212> TYPE: DNA
<213> ORGANISM: Homo sapiens

<400> SEQUENCE: 77

```
ctaaatcaag ctggagtcat gagggtagtg ggctaagtcg agggtccagc ctcttctgcc       60
aggaagccct tcttgctttt gagagagggc tgtgaccacc ccccatcctt ctccctacac      120
tcccagccaa cctagtgccc aagcagctaa acttggcttc cttctaatcc tggaaaaccc      180
tgtacccctc ctcctcaatc tggccctctc cacatgcaca ccctgagaac acacacagac      240
acacaacaca cacacataca caccctgaa cacacacaca gacacacata cacccatgat      300
gtgagcaaac acacacacgt gcgccttcat agcccagcca aggcatcgca ggcagggtgt      360
gctgcctgag atggcaccte cctttcagcc attcttcaag aatgggccac acacagctag      420
aagtcctctc ccagctagaa gtcctgtccc actctcctgg cctgacaaga tgagctctcc      480
tgggaccttg ctctagggca ctctgcctct accctaggac actggaatgc cctgggagcc      540
ccctccctgc aaccagcctg agttcagccc cacggacaaa gggacacaca gcccccaatg      600
gagaccattg taagtggtgg ggctgggaga ggaggaacag aaggaaagcc atagcgctct      660 cttgccctt ggcatgtacc ccaaggcctg atggccactg ggctcagcct gtcccccact      720
cctgcctgct tcccggtgag ctgccccga cacgtgcagc ccgggctgcc tccagggtct      780
ggctgagtgg gatcaggtgg ccctccaact cagcacagga aataagtaga aacatttcag      840
caggccacct cccctcatct tccccgcccct gtccagcgcc ctggcaaagg ctgacaactg      900
gctgtcttgg ggccgaacag ccctgcctgc tctgagggcc acagcctgtg ctgcataccc      960
accgcccagc ttctccctga gggcccacca gcctgtgctg catacccacc cccagcttc     1020 tccctgaggg cccaccagcc tgtgctgtac accccgttag tccctgatcc caaccttctc     1080
cctcctgcca gcacaccgat gcacacaccg gaagtggcga gccaagccc tggggacagg      1140 tgtagggaga aaagcagccc caggcctcag actcgctctc ccatcactgg catagagtgg     1200
gaggatggct ggagggtgtc tataggtaca gcccgctctg gctgctgcca ggtgggcccc     1260 tgccagggt cctcacccct gtccaccctg tgcctggctg tccctgcacc cagatacagc      1320
aacatggcct gtacccagca gagtggtggc aaccaccatg gttacagcgg atgccccgag     1380
actctgcttg gtaaacgtgg cagagcagaa tgggaggctg ggaccctgag gaagggcccc     1440
tctcctggca tctgtctctt gctacctaag cctgtgcctc tccctaaaga gctgcctccc     1500
```

```
tgctgccgag ccctggtctg gccacgagcc actactgcct cccacaggca ccactgcctc    1560
ccgctgctgc ccacaggtgg tgccgccaat gggcagtgcc tccaggccga agccttcaat    1620
cccccatctt gagccaggc ctaaatcctc ttaatagtga tggttggttt tgtcctccca    1680
ttaactgcag gtgggatttc cacctggggg aatgaggctt gcgttgttcg ggcgtctgct    1740
ggccctgaga catccagtct tccacactca actgtggat gggagggtgg cgtggcttta    1800
ccccatggag gctgttccag ggctctgggc acacagctgt gctcacacaa aatactgggt    1860
ggcttggttt agagctaatt gtagtggaag cctgcaaggt tgagggtga aggggagggg    1920 gcttgcaagg tccaggtaaa gatctggaaa gacagaacgt acagcttgga gggcaagggg    1980
gactctaaag tgcaaggaga tttacagttg ggaaaggagg cagtggcaga ggggttgagg    2040
gacaggggcc cttaagtcca gcgaggaaag ctcggtgtgg ggcccgctct acgctccgtt    2100
tggggtgacc tggaacgcct cttctcccag ctccctccag ccatcagcag cctcttgtca    2160
agcttctgcc tcgcccagt ctatccccaa ccccaaatca agaccacctt tcttcaacgg    2220
tcactattta ttcttgttc cttttctttt tgtgtaagaa acattcacaa aaaccagtgc    2280
caaaaccatc aaaaaaaaaa aa                                              2302

<210> SEQ ID NO 78
<211> LENGTH: 1729
<212> TYPE: DNA
<213> ORGANISM: Homo sapiens

<400> SEQUENCE: 78
tggccagaga tgcctgccca cagcctggtg atgagcagcc cggccctccc ggccttcctg      60
ctctgcagca cgctgctggt catcaagatg tacgtggtgg ccatcatcac gggccaagtg     120
aggctgcgga agaaggcctt tgccaaccc gaggatgccc tgagacacgg aggaggcccc      180
cagtattgca ggagcgaccc cgacgtggaa cgctgcctca gggcccaccg gaacgacatg     240
gagaccatct accccttcct tttcctgggc ttcgtctact cctttctggg tcctaacct      300 tttgtcgcct ggatgcactt cctggtcttc ctcgtgggcc gtgtggcaca caccgtggcc    360
tacctgggga gctgcgggc acccatccgc tccgtgacct acaccctggc ccagctcccc    420
tgcgcctcca tggctctgca gatcctctgg gaagcggccc gccacctgtg accagcagct   480
gatgcctcct tggccaccag accatgggcc aagagccgcc gtggctatac ctggggactt    540
gatgttcctt ccagattgtg gtgtgggccc tgagtcctgg tttcctggca gcctgctgcg    600
cgtgtgggtc tctgggcaca gtgggcctgt gtgtgtgccc gtgtgtgtgt atgtgtgtgt    660 gtatgttct tagccccttg gattcctgca cgaagtggct gatgggaacc atttcaagac    720
agattgtgaa gattgataga aaatccttca gctaaagtaa cagagcatca aaaacatcac    780
tccctctccc tccctaacag tgaaaagaga gaagggagac tctatttaag attcccaaac    840
ctaatgatca tctgaatccc gggctaagaa tgcagacttt tcagactgac cccagaaatt    900
ctggcccagc caatctagag gcaagcctgg ccatctgtat ttttttttc caagacagag    960 tcttgctctc gttgcccaag ctggagtgaa gtggtacaat ctggctcact gcagcctccg   1020
cctcccgggt tcaagcgatt ctcccgcctc agcctcctga gtagctggga ttacaggcgc   1080
gtatcaccat acccagctaa tttttgtatt tttagtagag acgggttcac catgttgccc   1140
aggagggtct cgaactcctg gcctcaagtg atccacgcct cggcctccca aagtgctggg   1200
atgacaggca tgaatcactg tgctcagcca ccatctggag tttaaaagga cctcccatgt   1260
```

-continued

```
gagtccctgt gtggccaggc cagggacccc tgccagttct atgtggaagc aaggctgggg    1320
tcttgggttc ctgtatggtg aagctgggt  gagccaagga cagggctggc tcctctgccc    1380
ccgctgacgc ttcccttgcc gttggctttg gatgtctttg ctgcagtctt ctctctggct    1440
caggtgtggg tgggaggggc ccacaggaag ctcagccttc tcctcccaag gtttgagtcc    1500
ctccaaaggg cagtgggtgg aggaccggga gctttgggtg accagccact caaaggaact    1560
ttctggtccc ttcagtatct tcaaggtttg gaaactgcaa atgtcccctg atggggaatc    1620
ctgtgtgtgt gtgtgtgtgt gtgtgtgtgt gtgtgtgtgt gtgtgtgttt tctcctagac    1680
ccgtgacctg agatgtgtga ttttagtca  ttaaatggaa gtgtctgcc                1729
```

<210> SEQ ID NO 79
<211> LENGTH: 136
<212> TYPE: PRT
<213> ORGANISM: Homo sapiens

<400> SEQUENCE: 79

```
Met Ser Asn Val Pro His Lys Ser Ser Leu Pro Glu Gly Ile Arg Pro
 1               5                  10                  15

Gly Thr Val Leu Arg Ile Arg Gly Leu Val Pro Pro Asn Ala Ser Arg
                20                  25                  30

Phe His Val Asn Leu Leu Cys Gly Glu Glu Gln Gly Ser Asp Ala Ala
            35                  40                  45

Leu His Phe Asn Pro Arg Leu Asp Thr Ser Glu Val Val Phe Asn Ser
        50                  55                  60

Lys Glu Gln Gly Ser Trp Gly Arg Glu Arg Gly Pro Gly Val Pro
65                  70                  75                  80

Phe Gln Arg Gly Gln Pro Phe Glu Val Leu Ile Ile Ala Ser Asp Asp
                85                  90                  95

Gly Phe Lys Ala Val Gly Asp Ala Gln Tyr His His Phe Arg His
                100                 105                 110

Arg Leu Pro Leu Ala Arg Val Arg Leu Val Glu Val Gly Gly Asp Val
            115                 120                 125

Gln Leu Asp Ser Val Arg Ile Phe
        130                 135
```

<210> SEQ ID NO 80
<211> LENGTH: 236
<212> TYPE: PRT
<213> ORGANISM: Homo sapiens

<400> SEQUENCE: 80

```
Met Ser Ala Pro Ser Ala Thr Pro Ile Phe Ala Pro Gly Glu Asn Cys
 1               5                  10                  15

Ser Pro Ala Trp Gly Ala Ala Pro Ala Ala Tyr Asp Ala Ala Asp Thr
                20                  25                  30

His Leu Arg Ile Leu Gly Lys Pro Val Met Glu Arg Trp Glu Thr Pro
            35                  40                  45

Tyr Met His Ala Leu Ala Ala Ala Ser Ser Lys Gly Gly Arg Val
        50                  55                  60

Leu Glu Val Gly Phe Gly Met Ala Ile Ala Ala Ser Lys Val Gln Glu
65                  70                  75                  80

Ala Pro Ile Asp Glu His Trp Ile Ile Glu Cys Asn Asp Gly Val Phe
                85                  90                  95

Gln Arg Leu Arg Asp Trp Ala Pro Arg Gln Thr His Lys Val Ile Pro
                100                 105                 110
```

```
Leu Lys Gly Leu Trp Glu Asp Val Ala Pro Thr Leu Pro Asp Gly His
        115                 120                 125

Phe Asp Gly Ile Leu Tyr Asp Thr Tyr Pro Leu Ser Glu Glu Thr Trp
130                 135                 140

His Thr His Gln Phe Asn Phe Ile Lys Asn His Ala Phe Arg Leu Leu
145                 150                 155                 160

Lys Pro Gly Gly Val Leu Thr Tyr Cys Asn Leu Thr Ser Trp Gly Glu
                165                 170                 175

Leu Met Lys Ser Lys Tyr Ser Asp Ile Thr Ile Met Phe Glu Glu Thr
            180                 185                 190

Gln Val Pro Ala Leu Leu Glu Ala Gly Phe Arg Arg Glu Asn Ile Arg
        195                 200                 205

Thr Glu Val Met Ala Leu Val Pro Pro Ala Asp Cys Arg Tyr Tyr Ala
    210                 215                 220

Phe Pro Gln Met Ile Thr Pro Leu Val Thr Lys Gly
225                 230                 235

<210> SEQ ID NO 81
<211> LENGTH: 322
<212> TYPE: PRT
<213> ORGANISM: Homo sapiens

<400> SEQUENCE: 81

Met Leu Ala Val His Phe Asp Lys Pro Gly Gly Pro Glu Asn Leu Tyr
1               5                   10                  15

Val Lys Glu Val Ala Lys Pro Ser Pro Gly Glu Gly Glu Val Leu Leu
            20                  25                  30

Lys Val Ala Ala Ser Ala Leu Asn Arg Ala Asp Leu Met Gln Arg Gln
        35                  40                  45

Gly Gln Tyr Asp Pro Pro Gly Ala Ser Asn Ile Leu Gly Leu Glu
    50                  55                  60

Ala Ser Gly His Val Ala Glu Leu Gly Pro Gly Cys Gln Gly His Trp
65                  70                  75                  80

Lys Ile Gly Asp Thr Ala Met Ala Leu Leu Pro Gly Gly Gly Gln Ala
                85                  90                  95

Gln Tyr Val Thr Val Pro Glu Gly Leu Leu Met Pro Ile Pro Glu Gly
            100                 105                 110

Leu Thr Leu Thr Gln Ala Ala Ile Pro Glu Ala Trp Leu Thr Ala
        115                 120                 125

Phe Gln Leu Leu His Leu Val Gly Asn Val Gln Ala Gly Asp Tyr Val
    130                 135                 140

Leu Ile His Ala Gly Leu Ser Gly Val Gly Thr Ala Ala Ile Gln Leu
145                 150                 155                 160

Thr Arg Met Ala Gly Ala Ile Pro Leu Val Thr Ala Gly Ser Gln Lys
                165                 170                 175

Lys Leu Gln Met Ala Glu Lys Leu Gly Ala Ala Gly Phe Asn Tyr
            180                 185                 190

Lys Lys Glu Asp Phe Ser Glu Ala Thr Leu Lys Phe Thr Lys Gly Ala
        195                 200                 205

Gly Val Asn Leu Ile Leu Asp Cys Ile Gly Gly Ser Tyr Trp Glu Lys
    210                 215                 220

Asn Val Asn Cys Leu Ala Leu Asp Gly Arg Trp Val Leu Tyr Gly Leu
225                 230                 235                 240

Met Gly Gly Gly Asp Ile Asn Gly Pro Leu Phe Ser Lys Leu Leu Phe
```

```
                    245                 250                 255
Lys Arg Gly Ser Leu Ile Thr Ser Leu Leu Arg Ser Arg Asp Asn Lys
            260                 265                 270

Tyr Lys Gln Met Leu Val Asn Ala Phe Thr Glu Gln Ile Leu Pro His
            275                 280                 285

Phe Ser Thr Glu Gly Pro Gln Arg Leu Leu Pro Val Leu Asp Arg Ile
            290                 295                 300

Tyr Pro Val Thr Glu Ile Gln Glu Ala His Ser Thr Trp Arg Pro Thr
305                 310                 315                 320

Arg Thr

<210> SEQ ID NO 82
<211> LENGTH: 122
<212> TYPE: PRT
<213> ORGANISM: Homo sapiens

<400> SEQUENCE: 82

Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
50                  55                  60

Arg Gly Pro Gly Gly Ala Trp Ala Ala Glu Val Ile Ser Asn Ala Arg
65                  70                  75                  80

Glu Asn Ile Gln Arg Leu Thr Gly His Gly Ala Glu Asp Ser Leu Ala
                85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120

<210> SEQ ID NO 83
<211> LENGTH: 253
<212> TYPE: PRT
<213> ORGANISM: Homo sapiens

<400> SEQUENCE: 83

Gly Ala Tyr Leu Ala Gln Glu Arg Ala Arg Ala Gln Ile Gly Tyr Glu
1               5                   10                  15

Asp Pro Ile Asn Pro Thr Tyr Glu Ala Thr Asn Ala Met Tyr His Arg
            20                  25                  30

Cys Leu Asp Tyr Val Leu Glu Glu Leu Lys His Asn Ala Lys Ala Lys
        35                  40                  45

Val Met Val Ala Ser His Asn Glu Asp Thr Val Arg Phe Ala Leu Arg
50                  55                  60

Arg Met Glu Glu Leu Gly Leu His Pro Ala Asp His Gln Val Tyr Phe
65                  70                  75                  80

Gly Gln Leu Leu Gly Met Cys Asp Gln Ile Ser Phe Pro Leu Gly His
                85                  90                  95

Gly Trp Leu Pro Arg Val Gln Val Arg Ala Leu Trp Pro Arg Asp Gly
            100                 105                 110

Gly Ala Ala Leu Leu Val Pro Ala Val Pro Trp Lys Asn Ser Ser Leu
        115                 120                 125
```

-continued

```
Met Lys Gly Thr His Ser Gly Ala Ala Leu Ala Val Ala Gly Ala Leu
    130                 135                 140

Glu Ala Ala Pro Asn Trp Gln Pro Leu Pro Ser Pro Cys Leu Ala Pro
145                 150                 155                 160

Ala Ser Thr Pro Ser Ser Leu Pro Ala Pro Ala Pro Cys Ser Arg
                165                 170                 175

Pro Phe Asn Gln Gln Ala Ala Ser Gln Thr Pro Ile Leu Gln His Arg
                180                 185                 190

Phe Thr Phe Phe His Pro Thr Thr Leu Gln Ser Leu Leu Gly Gly Glu
            195                 200                 205

Val Arg Cys Leu Pro Ala Leu Ala Gln Ser Met Gly Thr Gln Val Trp
    210                 215                 220

Ala Glu Pro Asp Thr Cys Leu Gly Gln Pro Leu Glu Thr Phe Gly Asn
225                 230                 235                 240

Ser Pro Leu Lys Cys Val Gly Pro Arg Pro Pro Leu
                245                 250

<210> SEQ ID NO 84
<211> LENGTH: 228
<212> TYPE: PRT
<213> ORGANISM: Homo sapiens

<400> SEQUENCE: 84

Met Ser Val Pro Gly Pro Tyr Gln Ala Ala Thr Gly Pro Ser Ser Ala
1               5                   10                  15

Pro Ser Ala Pro Pro Ser Tyr Glu Glu Thr Val Ala Val Asn Ser Tyr
            20                  25                  30

Tyr Pro Thr Pro Pro Ala Pro Met Pro Gly Pro Thr Thr Gly Leu Val
        35                  40                  45

Thr Gly Pro Asp Gly Lys Gly Met Asn Pro Pro Ser Tyr Tyr Thr Gln
    50                  55                  60

Pro Ala Pro Ile Pro Asn Asn Asn Pro Ile Thr Val Gln Thr Val Tyr
65                  70                  75                  80

Val Gln His Pro Ile Thr Phe Leu Asp Arg Pro Ile Gln Met Cys Cys
                85                  90                  95

Pro Ser Cys Asn Lys Met Ile Val Ser Gln Leu Ser Tyr Asn Ala Gly
                100                 105                 110

Ala Leu Thr Trp Leu Ser Cys Gly Ser Leu Cys Leu Leu Gly Val His
            115                 120                 125

Ser Gly Leu Leu Leu His Pro Leu Leu Arg Gly Cys Pro Ala Gly Arg
130                 135                 140

Gly Pro Leu Leu Ser Gln Leu Gln Ser Ser Pro Gly His Leu Gln Ala
145                 150                 155                 160

Phe Val Gly Leu Ser Gln Thr Trp Arg Glu Pro Gly Ala Ala Gly Ser
                165                 170                 175

Pro Phe His Leu Ser Ser Phe Thr Pro Gly Gly Ser Ala Leu
            180                 185                 190

Val Val Ser Pro Leu Gln Gly Ala His Leu His Val Phe Phe Trp Gly
        195                 200                 205

Glu Tyr Val Ala Lys Leu Thr Asn Leu Gln Thr Pro Glu Ile Ala Ala
    210                 215                 220

Trp Ser Arg Ala
225
```

-continued

```
<210> SEQ ID NO 85
<211> LENGTH: 803
<212> TYPE: PRT
<213> ORGANISM: Homo sapiens

<400> SEQUENCE: 85
```

| | | | | | | | | | | | | | | |
|---|---|---|---|---|---|---|---|---|---|---|---|---|---|---|
| Met | Glu | Asp | Leu | Gly | Glu | Asn | Thr | Met | Val | Leu | Ser | Thr | Leu | Arg | Ser |
| 1 | | | | 5 | | | | | 10 | | | | | 15 | |
| Leu | Asn | Asn | Phe | Ile | Ser | Gln | Arg | Val | Glu | Gly | Ser | Gly | Leu | Asp | |
| | | | 20 | | | | | 25 | | | | | 30 | | |
| Ile | Ser | Thr | Ser | Ala | Pro | Gly | Ser | Leu | Gln | Met | Gln | Tyr | Gln | Gln | Ser |
| | | | 35 | | | | | 40 | | | | | 45 | | |
| Met | Gln | Leu | Glu | Glu | Arg | Ala | Glu | Gln | Ile | Arg | Ser | Lys | Ser | His | Leu |
| | 50 | | | | | 55 | | | | | 60 | | | | |
| Ile | Gln | Val | Glu | Arg | Glu | Lys | Met | Gln | Met | Glu | Leu | Ser | His | Lys | Arg |
| 65 | | | | | 70 | | | | | 75 | | | | | 80 |
| Ala | Arg | Val | Glu | Leu | Glu | Arg | Ala | Ala | Ser | Thr | Ser | Ala | Arg | Asn | Tyr |
| | | | | 85 | | | | | 90 | | | | | 95 | |
| Glu | Arg | Glu | Val | Asp | Arg | Asn | Gln | Glu | Leu | Leu | Thr | Arg | Ile | Arg | Gln |
| | | | 100 | | | | | 105 | | | | | 110 | | |
| Leu | Gln | Glu | Arg | Glu | Ala | Gly | Ala | Glu | Glu | Lys | Met | Gln | Glu | Gln | Leu |
| | | | 115 | | | | | 120 | | | | | 125 | | |
| Glu | Arg | Asn | Arg | Gln | Cys | Gln | Gln | Asn | Leu | Asp | Ala | Ala | Ser | Lys | Arg |
| | 130 | | | | | 135 | | | | | 140 | | | | |
| Leu | Arg | Glu | Lys | Glu | Asp | Ser | Leu | Ala | Gln | Ala | Gly | Glu | Thr | Ile | Asn |
| 145 | | | | | 150 | | | | | 155 | | | | | 160 |
| Ala | Leu | Lys | Gly | Arg | Ile | Ser | Glu | Leu | Gln | Trp | Ser | Val | Met | Asp | Gln |
| | | | | 165 | | | | | 170 | | | | | 175 | |
| Glu | Met | Arg | Val | Lys | Arg | Leu | Glu | Ser | Glu | Lys | Gln | Asp | Val | Gln | Glu |
| | | | 180 | | | | | 185 | | | | | 190 | | |
| Gln | Leu | Asp | Leu | Gln | His | Lys | Lys | Cys | Gln | Glu | Ala | Asn | Gln | Lys | Ile |
| | | | 195 | | | | | 200 | | | | | 205 | | |
| Gln | Glu | Leu | Gln | Ala | Ser | Gln | Glu | Ala | Arg | Ala | Asp | His | Glu | Gln | Gln |
| | 210 | | | | | 215 | | | | | 220 | | | | |
| Ile | Lys | Asp | Leu | Glu | Gln | Lys | Leu | Ser | Leu | Gln | Glu | Gln | Asp | Ala | Ala |
| 225 | | | | | 230 | | | | | 235 | | | | | 240 |
| Ile | Val | Lys | Asn | Met | Lys | Ser | Glu | Leu | Val | Arg | Leu | Pro | Arg | Leu | Glu |
| | | | | 245 | | | | | 250 | | | | | 255 | |
| Arg | Glu | Leu | Glu | Gln | Leu | Arg | Glu | Glu | Ser | Ala | Leu | Arg | Glu | Met | Arg |
| | | | 260 | | | | | 265 | | | | | 270 | | |
| Glu | Thr | Asn | Gly | Leu | Leu | Gln | Glu | Glu | Leu | Gly | Leu | Gln | Arg | Lys | |
| | | | 275 | | | | | 280 | | | | | 285 | | |
| Leu | Gly | Arg | Gln | Glu | Lys | Met | Gln | Glu | Thr | Leu | Val | Gly | Leu | Glu | Leu |
| | | | 290 | | | | | 295 | | | | | 300 | | |
| Glu | Asn | Glu | Arg | Leu | Leu | Ala | Lys | Leu | Gln | Ser | Trp | Glu | Arg | Leu | Asp |
| 305 | | | | | 310 | | | | | 315 | | | | | 320 |
| Gln | Thr | Met | Gly | Leu | Ser | Ile | Arg | Thr | Pro | Glu | Asp | Leu | Ser | Arg | Phe |
| | | | | 325 | | | | | 330 | | | | | 335 | |
| Val | Val | Glu | Leu | Gln | Gln | Arg | Glu | Leu | Ala | Leu | Lys | Asp | Lys | Asn | Ser |
| | | | 340 | | | | | 345 | | | | | 350 | | |
| Ala | Val | Thr | Ser | Ser | Ala | Arg | Gly | Leu | Glu | Lys | Ala | Arg | Gln | Gln | Leu |
| | | | 355 | | | | | 360 | | | | | 365 | | |
| Gln | Glu | Glu | Leu | Arg | Gln | Val | Ser | Gly | Gln | Leu | Leu | Glu | Glu | Arg | Lys |
| | 370 | | | | | 375 | | | | | 380 | | | | |

-continued

```
Lys Arg Glu Thr His Glu Ala Leu Ala Arg Arg Leu Gln Lys Arg Val
385                 390                 395                 400

Leu Leu Leu Thr Lys Glu Arg Asp Gly Met Arg Ala Ile Leu Gly Ser
            405                 410                 415

Tyr Asp Ser Glu Leu Thr Pro Ala Glu Tyr Ser Pro Gln Leu Thr Arg
        420                 425                 430

Arg Met Arg Glu Ala Glu Asp Met Val Gln Lys Val His Ser His Ser
    435                 440                 445

Ala Glu Met Glu Ala Gln Leu Ser Gln Ala Leu Glu Glu Leu Gly Gly
450                 455                 460

Gln Lys Gln Arg Ala Asp Met Leu Glu Met Glu Leu Lys Met Leu Lys
465                 470                 475                 480

Ser Gln Ser Ser Ser Ala Glu Gln Ser Phe Leu Phe Ser Arg Glu Glu
                485                 490                 495

Ala Asp Thr Leu Arg Leu Lys Val Glu Glu Leu Glu Gly Glu Arg Ser
            500                 505                 510

Arg Leu Glu Glu Glu Lys Arg Met Leu Glu Ala Gln Leu Glu Arg Arg
        515                 520                 525

Ala Leu Gln Gly Asp Tyr Asp Gln Ser Arg Thr Lys Val Leu His Met
530                 535                 540

Ser Leu Asn Pro Thr Ser Val Ala Arg Gln Arg Leu Arg Glu Asp His
545                 550                 555                 560

Ser Gln Leu Gln Ala Glu Cys Glu Arg Leu Arg Gly Leu Leu Arg Ala
                565                 570                 575

Met Glu Arg Gly Gly Thr Val Pro Ala Asp Leu Glu Ala Ala Ala Ala
            580                 585                 590

Ser Leu Pro Ser Ser Lys Glu Val Ala Glu Leu Lys Lys Gln Val Glu
        595                 600                 605

Ser Ala Glu Leu Lys Asn Gln Arg Leu Lys Glu Val Phe Gln Thr Lys
610                 615                 620

Ile Gln Glu Phe Arg Lys Ala Cys Tyr Thr Leu Thr Gly Tyr Gln Ile
625                 630                 635                 640

Asp Ile Thr Thr Glu Asn Gln Tyr Arg Leu Thr Ser Leu Tyr Ala Glu
                645                 650                 655

His Pro Gly Asp Cys Ser Ser Arg Pro Ala Pro Arg Val Pro
            660                 665                 670

Arg Cys Ser Tyr Trp Arg Gln Ser Ser His Thr Pro Trp Ala Ser Ser
        675                 680                 685

Ser Arg Cys Thr Cys Gly Ala Arg Thr Ala Ser Leu Pro Ser Ser Ala
        690                 695                 700

Arg Ser Pro Ser Ser Ser Ala Ala Arg Pro Trp Arg Ser Leu Gln
705                 710                 715                 720

Ala Arg Gly His Ser Arg Ser His Ser Ala Trp Pro Asp Leu Gln Val
            725                 730                 735

Pro Cys Pro Ala Ser His Arg Leu Gly Ala Arg Pro Ala Ser Pro Ala
        740                 745                 750

Pro Gln Gly Ser Ser Met Thr Asp Arg His Ala Gly Thr Tyr Val Gly
        755                 760                 765

Leu Pro Ala Gly Ala Ala Ser Thr Leu Ser Thr Cys Arg Pro His Ala
    770                 775                 780

Ser Arg Ser Leu Val Cys Gly Arg Arg Pro Ala Trp Val Pro His
785                 790                 795                 800

Leu Val Lys
```

<210> SEQ ID NO 86
<211> LENGTH: 516
<212> TYPE: PRT
<213> ORGANISM: Homo sapiens

<400> SEQUENCE: 86

Met Ser Val Ser Val His Glu Asn Arg Lys Ser Arg Ala Ser Ser Gly
 1               5                  10                  15

Ser Ile Asn Ile Tyr Leu Phe His Lys Ser Ser Tyr Ala Asp Ser Val
            20                  25                  30

Leu Thr His Leu Asn Leu Leu Arg Gln Gln Arg Leu Phe Thr Asp Val
        35                  40                  45

Leu Leu His Ala Gly Asn Arg Thr Phe Pro Cys His Arg Ala Val Leu
    50                  55                  60

Ala Ala Cys Ser Arg Tyr Phe Glu Ala Met Phe Ser Gly Gly Leu Lys
65                  70                  75                  80

Glu Ser Gln Asp Ser Glu Val Asn Phe Asp Asn Ser Ile His Pro Glu
                85                  90                  95

Val Leu Glu Leu Leu Asp Tyr Ala Tyr Ser Ser Arg Val Ile His
            100                 105                 110

Gln Leu Glu Gly Lys Cys Arg Asn Ser Leu Leu Gly Ser Leu Val Thr
        115                 120                 125

Cys Trp Ser Phe Lys Asp Ile Arg Asp Ala Cys Ala Glu Phe Leu Glu
    130                 135                 140

Lys Asn Leu His Pro Thr Asn Cys Leu Gly Met Leu Leu Ser Asp
145                 150                 155                 160

Ala His Gln Cys Thr Lys Leu Tyr Glu Leu Ser Trp Arg Met Cys Leu
                165                 170                 175

Ser Asn Phe Gln Thr Ile Arg Lys Asn Glu Asp Phe Leu Gln Leu Pro
            180                 185                 190

Gln Asp Met Val Val Gln Leu Leu Ser Ser Glu Glu Leu Glu Thr Glu
        195                 200                 205

Asp Glu Arg Leu Val Tyr Glu Ser Ala Ile Asn Trp Ile Ser Tyr Asp
    210                 215                 220

Leu Lys Lys Arg Tyr Cys Tyr Leu Pro Glu Leu Leu Gln Thr Val Thr
225                 230                 235                 240

Arg Ala Leu Leu Pro Ala Ile Tyr Leu Met Glu Asn Val Ala Met Glu
                245                 250                 255

Glu Leu Ile Thr Lys Gln Arg Lys Ser Lys Glu Ile Val Glu Glu Ala
            260                 265                 270

Ile Arg Cys Lys Leu Lys Ile Leu Gln Asn Asp Gly Val Val Thr Ser
        275                 280                 285

Leu Cys Ala Arg Pro Arg Lys Thr Gly His Ala Leu Phe Leu Leu Gly
    290                 295                 300

Gly Gln Thr Phe Met Cys Asp Lys Leu Tyr Leu Val Asp Gln Lys Ala
305                 310                 315                 320

Lys Glu Ile Ile Pro Lys Ala Asp Ile Pro Ser Pro Arg Lys Glu Phe
                325                 330                 335

Ser Ala Cys Ala Ile Gly Cys Lys Val Tyr Ile Thr Gly Gly Arg Gly
            340                 345                 350

Ser Glu Asn Gly Val Ser Lys Asp Val Trp Val Tyr Asp Thr Leu His
        355                 360                 365

Glu Glu Trp Ser Lys Ala Ala Pro Met Leu Val Ala Arg Phe Gly His

```
            370             375             380
Gly Ser Ala Glu Leu Lys His Cys Leu Tyr Val Val Gly His Thr
385                 390                 395                 400

Ala Ala Thr Gly Cys Leu Pro Ala Ser Pro Ser Val Ser Leu Lys Gln
                405                 410                 415

Val Glu His Tyr Asp Pro Thr Ile Asn Lys Trp Thr Met Ala Ala Pro
                420                 425                 430

Arg Pro Arg Arg Tyr Asn Cys Ala Gln Val Val Ser Ala Lys Leu
            435                 440                 445

Lys Leu Phe Ala Phe Gly Gly Thr Ser Val Ser His Asp Lys Leu Pro
450                 455                 460

Lys Val Gln Cys Tyr Asp Gln Cys Glu Asn Arg Trp Thr Val Pro Ala
465                 470                 475                 480

Thr Cys Pro Gln Pro Trp Arg Ile His Ser Gln Ala Ser Cys Pro Gly
                485                 490                 495

Gly Thr Gln Asp Phe Leu Leu Trp Gly Val Ile Gln Asn Phe Ser Ala
                500                 505                 510

Cys Phe Cys Leu
        515

<210> SEQ ID NO 87
<211> LENGTH: 153
<212> TYPE: PRT
<213> ORGANISM: Homo sapiens

<400> SEQUENCE: 87

Met Pro Ala His Ser Leu Val Met Ser Ser Pro Ala Leu Pro Ala Phe
1               5                   10                  15

Leu Leu Cys Ser Thr Leu Leu Val Ile Lys Met Tyr Val Val Ala Ile
                20                  25                  30

Ile Thr Gly Gln Val Arg Leu Arg Lys Lys Ala Phe Ala Asn Pro Glu
            35                  40                  45

Asp Ala Leu Arg His Gly Gly Gly Pro Gln Tyr Cys Arg Ser Asp Pro
        50                  55                  60

Asp Val Glu Arg Cys Leu Arg Ala His Arg Asn Asp Met Glu Thr Ile
65                  70                  75                  80

Tyr Pro Phe Leu Phe Leu Gly Phe Val Tyr Ser Phe Leu Gly Pro Asn
                85                  90                  95

Pro Phe Val Ala Trp Met His Phe Leu Val Phe Leu Val Gly Arg Val
                100                 105                 110

Ala His Thr Val Ala Tyr Leu Gly Lys Leu Arg Ala Pro Ile Arg Ser
            115                 120                 125

Val Thr Tyr Thr Leu Ala Gln Leu Pro Cys Ala Ser Met Ala Leu Gln
        130                 135                 140

Ile Leu Trp Glu Ala Ala Arg His Leu
145                 150

<210> SEQ ID NO 88
<211> LENGTH: 155
<212> TYPE: PRT
<213> ORGANISM: Rat

<400> SEQUENCE: 88

Met Ala Asp Leu Lys Gln Leu Met Asp Asn Glu Val Leu Met Ala Phe
1               5                   10                  15

Thr Ser Tyr Ala Thr Ile Ile Leu Ala Lys Met Met Phe Leu Ser Ser
```

```
            20                  25                  30
Ala Thr Ala Phe Gln Arg Leu Thr Asn Lys Val Phe Ala Asn Pro Glu
            35                  40                  45

Asp Cys Ala Gly Phe Gly Lys Gly Glu Asn Ala Lys Lys Phe Leu Arg
    50                  55                  60

Thr Asp Glu Lys Val Glu Arg Val Arg Arg Ala His Leu Asn Asp Leu
65                  70                  75                  80

Glu Asn Ile Val Pro Phe Leu Gly Ile Gly Leu Leu Tyr Ser Leu Ser
                85                  90                  95

Gly Pro Asp Leu Ser Thr Ala Leu Ile His Phe Arg Ile Phe Val Gly
                100                 105                 110

Ala Arg Ile Tyr His Thr Ile Ala Tyr Leu Thr Pro Leu Pro Gln Pro
                115                 120                 125

Asn Arg Gly Leu Ala Phe Phe Val Gly Tyr Gly Val Thr Leu Ser Met
            130                 135                 140

Ala Tyr Arg Leu Leu Arg Ser Arg Leu Tyr Leu
145                 150                 155

<210> SEQ ID NO 89
<211> LENGTH: 324
<212> TYPE: PRT
<213> ORGANISM: Vigna

<400> SEQUENCE: 89

Met Val Lys Ala Ile Arg Val His Glu Gln Gly Pro Gln Val Leu
1               5                   10                  15

Lys Trp Glu Asp Val Glu Ile Gly Glu Pro Lys Glu Gly Glu Val Arg
            20                  25                  30

Val Arg Asn Lys Ala Val Gly Val Asn Phe Ile Asp Val Tyr Phe Arg
            35                  40                  45

Lys Gly Val Tyr Lys Pro Pro Ser Phe Pro Phe Thr Pro Gly Met Glu
    50                  55                  60

Ala Val Gly Val Val Thr Ala Val Gly Ala Gly Leu Thr Gly Arg Gln
65                  70                  75                  80

Val Gly Asp Leu Val Ala Tyr Ala Gly Gln Pro Met Gly Ser Tyr Ala
                85                  90                  95

Glu Glu Gln Ile Leu Pro Ala Asn Lys Val Pro Val Pro Ser Ser
                100                 105                 110

Ile Asp Pro Pro Ile Ala Ala Ser Ile Met Leu Lys Gly Met Thr Thr
            115                 120                 125

His Phe Leu Val Arg Arg Cys Phe Lys Val Glu Pro Gly His Thr Ile
            130                 135                 140

Leu Val His Ala Ala Gly Val Gly Ser Leu Leu Cys Gln Trp
145                 150                 155                 160

Ala Asn Ala Leu Gly Ala Thr Val Ile Gly Thr Val Ser Asn Lys Glu
                165                 170                 175

Lys Ala Ala Gln Ala Lys Glu Asp Gly Cys His His Val Ile Ile Tyr
                180                 185                 190

Lys Glu Glu Asp Phe Val Ala Arg Val Asn Glu Ile Thr Ser Gly Asn
            195                 200                 205

Gly Val Glu Val Val Tyr Asp Ser Val Gly Lys Asp Thr Phe Glu Gly
            210                 215                 220

Ser Leu Ala Cys Leu Lys Leu Arg Gly Tyr Met Val Ser Phe Gly Gln
225                 230                 235                 240
```

Ser Ser Gly Ser Pro Asp Pro Val Pro Leu Ser Ser Leu Ala Ala Lys
            245                 250                 255

Ser Leu Phe Leu Thr Arg Pro Ser Leu Met Gln Tyr Val Val Thr Arg
            260                 265                 270

Asp Glu Leu Leu Glu Ala Ala Gly Glu Leu Phe Ala Asn Val Ala Ser
            275                 280                 285

Gly Val Leu Lys Val Arg Val Asn His Thr Tyr Pro Leu Ser Glu Ala
            290                 295                 300

Ala Lys Ala His Glu Asp Leu Glu Asn Arg Lys Thr Ser Gly Ser Ile
305                 310                 315                 320

Val Leu Ile Pro

<210> SEQ ID NO 90
<211> LENGTH: 359
<212> TYPE: PRT
<213> ORGANISM: Homo sapiens

<400> SEQUENCE: 90

Met Ile Trp Gly His Phe Ser Leu Leu Cys Val Val Asp Ser Leu Gly
  1               5                  10                  15

Gly Glu Glu Met Ala Asp Ser Val Lys Thr Phe Leu Gln Asp Leu Ala
            20                  25                  30

Arg Gly Ile Lys Asp Ser Ile Trp Gly Ile Cys Thr Ile Ser Lys Leu
            35                  40                  45

Asp Ala Arg Ile Gln Gln Lys Arg Glu Gln Arg Arg Arg Ala
 50                  55                  60

Ser Ser Val Leu Ala Gln Arg Arg Pro Gln Ser Ile Glu Arg Lys Gln
 65                  70                  75                  80

Glu Ser Glu Pro Arg Ile Val Ser Arg Ile Phe Gln Cys Cys Ala Trp
            85                  90                  95

Asn Gly Gly Val Phe Trp Phe Ser Leu Leu Phe Tyr Arg Val Phe
            100                 105                 110

Ile Pro Val Leu Gln Ser Val Thr Ala Arg Ile Ile Gly Asp Pro Ser
            115                 120                 125

Leu His Gly Asp Val Trp Ser Trp Leu Gly Phe Phe Leu Thr Ser Ile
            130                 135                 140

Phe Ser Ala Val Trp Val Leu Pro Leu Phe Val Leu Ser Lys Val Val
145                 150                 155                 160

Asn Ala Ile Trp Phe Gln Asp Ile Ala Asp Leu Ala Phe Glu Val Ser
            165                 170                 175

Gly Arg Lys Pro His Pro Phe Pro Ser Val Ser Lys Ile Ile Ala Asp
            180                 185                 190

Met Leu Phe Asn Leu Leu Gln Ala Leu Phe Leu Ile Gln Gly Met
            195                 200                 205

Phe Val Ser Leu Phe Pro Ile His Leu Val Gly Gln Leu Val Ser Leu
            210                 215                 220

Leu His Met Ser Leu Leu Tyr Ser Leu Tyr Cys Phe Glu Tyr Arg Trp
225                 230                 235                 240

Phe Asn Lys Gly Ile Glu Met His Gln Arg Leu Ser Asn Ile Glu Arg
            245                 250                 255

Asn Trp Pro Tyr Tyr Phe Gly Phe Gly Leu Pro Leu Ala Phe Leu Thr
            260                 265                 270

Ala Met Gln Ser Ser Tyr Ile Ile Ser Gly Cys Leu Phe Ser Ile Leu
            275                 280                 285

-continued

Phe Pro Leu Phe Ile Ile Ser Ala Asn Glu Ala Lys Thr Pro Gly Lys
          290                 295                 300

Ala Tyr Leu Phe Gln Leu Arg Leu Phe Ser Leu Val Phe Leu Ser
305                 310                 315                 320

Asn Arg Leu Phe His Lys Thr Val Tyr Leu Gln Ser Ala Leu Ser Ser
                      325                 330                 335

Ser Thr Ser Ala Glu Lys Phe Pro Ser Pro His Pro Ser Pro Ala Lys
                340                 345                 350

Leu Lys Ala Thr Ala Gly His
          355

<210> SEQ ID NO 91
<211> LENGTH: 315
<212> TYPE: PRT
<213> ORGANISM: C. elegans

<400> SEQUENCE: 91

Met Val Lys Phe Gln Ile Ile Ala Arg Asp Phe Tyr His Gly Phe Ile
1               5                   10                  15

Asp Ser Phe Lys Gly Ile Thr Phe Val Arg Arg Ile Arg Glu Glu
            20                  25                  30

Ala Lys Glu Val Lys Val Glu Pro Pro Lys Pro Val Glu Arg Thr Val
            35                  40                  45

Leu Met Met Arg Arg Glu Lys Gln Gly Ile Phe Lys Arg Pro Pro Glu
50                  55                  60

Pro Pro Lys Lys Lys Asp Ser Phe Leu Lys Lys Leu Trp Gln Ile Tyr
65                  70                  75                  80

Ala Met Asn Ile Gly Phe Leu Val Leu Trp Gln Val Cys Ile Leu Ile
                85                  90                  95

Leu Gly Leu Phe Phe Ser Phe Phe Asp Arg Thr Asp Leu Gly His Asn
                100                 105                 110

Ile Gly Tyr Ile Leu Ile Ile Pro Ile Phe Phe Ala Ser Arg Ile Ile
            115                 120                 125

Gln Ala Leu Trp Phe Ser Asp Ile Ser Gly Ala Cys Met Arg Ala Leu
    130                 135                 140

Lys Leu Pro Pro Pro Val Val Pro Phe Ser Ser Met Leu Ala Gly
145                 150                 155                 160

Thr Leu Ile Ser Ala Leu His Gln Ile Phe Phe Leu Ile Gln Gly Met
                165                 170                 175

Leu Ser Gln Tyr Leu Pro Ile Pro Leu Ile Thr Pro Val Ile Val Tyr
            180                 185                 190

Leu His Met Ala Leu Leu Asn Ser Met Tyr Cys Phe Asp Tyr Phe Phe
    195                 200                 205

Asp Gly Tyr Asn Leu Ser Phe Leu Arg Arg Lys Asp Ile Phe Glu Ser
210                 215                 220

His Trp Pro Tyr Phe Leu Gly Phe Gly Thr Pro Leu Ala Leu Ala Cys
225                 230                 235                 240

Ser Ile Ser Ser Asn Met Phe Val Asn Ser Val Ile Phe Ala Leu Leu
                245                 250                 255

Phe Pro Phe Phe Ile Ile Thr Ser Tyr Pro Ala Asn Trp Asn Arg Lys
            260                 265                 270

Tyr Glu Glu Glu Ile Pro Lys Ile Ala Phe Cys Arg Ile Ser Tyr Met
        275                 280                 285

Phe Thr Glu Leu Val Gly Lys Phe Val Lys Ser Ile Thr Pro Thr Asn
    290                 295                 300

```
Asn Pro Thr Ala Ala Arg Asn Asn Ala Gln Asn
305                 310                 315

<210> SEQ ID NO 92
<211> LENGTH: 83
<212> TYPE: PRT
<213> ORGANISM: Homo sapiens

<400> SEQUENCE: 92

Ile Gly Tyr Glu Asp Pro Ile Asn Pro Thr Tyr Glu Ala Thr Asn Ala
1               5                   10                  15

Met Tyr His Arg Cys Leu Asp Tyr Val Leu Glu Glu Leu Lys His Asn
            20                  25                  30

Ala Lys Ala Lys Val Met Val Ala Ser His Asn Glu Asp Thr Val Arg
        35                  40                  45

Phe Ala Leu Arg Arg Met Glu Glu Leu Gly Leu His Pro Ala Asp His
    50                  55                  60

Gln Val Tyr Phe Gly Gln Leu Leu Gly Met Cys Asp Gln Ile Ser Phe
65                  70                  75                  80

Pro Leu Gly

<210> SEQ ID NO 93
<211> LENGTH: 89
<212> TYPE: PRT
<213> ORGANISM: Drosophila

<400> SEQUENCE: 93

Ile Gly Tyr Glu Asp Pro Val Asn Pro Thr Phe Glu Ala Thr Thr Asp
1               5                   10                  15

Met Tyr His Arg Leu Ser Glu Cys Leu Arg Arg Ile Lys Leu Met Lys
            20                  25                  30

Asp Cys Asp Asp Asp Ala Arg Lys Ile Gly Ile Met Val Ala Ser His
        35                  40                  45

Asn Glu Asp Thr Val Arg Phe Ala Ile Gln Gln Met Lys Glu Ile Gly
    50                  55                  60

Ile Ser Pro Glu Asp Lys Val Ile Cys Phe Gly Gln Leu Leu Gly Met
65                  70                  75                  80

Cys Asp Tyr Ile Thr Phe Pro Leu Gly
                85
```

US 6,432,640 B1

P53-INDUCED APOPTOSIS

This application claims the benefit of co-pending provisional applications Ser. No. 60/059,153 filed Sep. 17, 1997 and Ser. No. 60/079,817 filed Mar. 30, 1998. These two applications are incorporated by reference herein.

This invention was made using grant funds from the U.S. National Institutes of Health (CA57345). Therefore the government retains some rights in the present invention.

TECHNICAL FIELD OF THE INVENTION

This invention is related to genes and proteins involved in cell cycle control and tumorigenesis. These genes can be used diagnostically and therapeutically because of their role in cancers.

BACKGROUND OF THE INVENTION

The inactivation of the p53 gene in a large fraction of human cancers has inspired an intense search for the encoded protein's physiologic and biologic properties. Expression of p53 induces either a stable growth arrest or programmed cell death (apoptosis). In human colorectal cancers (CRC), the growth arrest is dependent on the transcriptional induction of p21WAF1/CIP1 (1), but the biochemical mechanisms underlying the development of p53-dependent apoptosis are largely unknown (2). Thus, there is a continuing need in the art for discovering new genes which are regulated by p53 and genes which are related to cell cycle control and tumorigenesis.

SUMMARY OF THE INVENTION

It is an object of the present invention to provide methods of diagnosing cancer or determining p53 status in a sample suspected of being neoplastic.

It is another object of the present invention to provide an isolated and purified nucleic acid molecule which is identified by a SAGE tag.

It is an object of the present invention to provide an isolated nucleotide probe comprising at least 12 nucleotides of a rat nucleic acid molecule identified by a SAGE tag.

Another object of the invention is to provide methods and kits for evaluating cytotoxicity or carcinogenicity of an agent.

It is still another object of the invention to provide a DNA construct useful for screening drugs as anti-neoplastic agents.

It is even another object of the invention to provide a preparation of antibodies.

These and other objects of the invention are provided by one or more of the embodiments described below. One embodiment of the invention provides a method of diagnosing cancer or determining p53 status in a sample suspected of being neoplastic. The level of transcription of an RNA transcript in a first sample of a first tissue is compared to the level of transcription of the transcript in a second sample of a second tissue. The first tissue is suspected of being neoplastic and the second tissue is a normal human tissue. The first and second tissue are of the same tissue type. The transcript is identified by a tag selected from the group consisting of SEQ ID NOS:10, 15–22, 26, 27, and 30. The first sample is characterized as neoplastic or as having a mutant p53 when transcription is found to be the same or lower in the first sample than in the second sample.

Another embodiment of the invention provides a method of diagnosing cancer or determining p53 status in a sample suspected of being neoplastic. The level of transcription of an RNA transcript in a first sample of a first tissue is compared to the level of transcription of the transcript in a second sample of a second tissue. The first tissue is suspected of being neoplastic, and the second tissue is a normal human tissue. The first and second tissue are of the same tissue type. The transcript is identified by a tag selected from the group consisting of SEQ ID NOS:37–67. The first sample is categorized as neoplastic or as having a mutant p53 when transcription is found to be the same or higher in the first sample than in the second sample.

Yet another embodiment of the invention provides an isolated and purified nucleic acid molecule which comprises a SAGE tag selected from the group consisting of SEQ ID NOS:15, 16, 17, 19, 21, 22, and 30.

Even another embodiment of the invention provides an isolated nucleotide probe comprising at least 12 contiguous nucleotides of a human nucleic acid molecule. The human nucleic acid molecule comprises a SAGE tag selected from the group consisting of SEQ ID NOS:15, 16, 17, 19, 21, 22, and 30.

A further embodiment of the invention provides a kit for evaluating toxicity or carcinogenicity of an agent. The kit comprises at least 2 probes. The probes comprise at least 12 contiguous nucleotides of a human nucleic acid molecule. The human nucleic acid molecule comprises a SAGE tag selected from the group consisting of SEQ ID NOS:15, 16, 17, 19, 21, 22, and 30.

Another embodiment of the invention provides a kit for evaluating cytotoxicity or carcinogenicity. The kit comprises at least 2 probes. The probes comprise a SAGE tag selected from the group consisting of SEQ ID NOS:15, 16, 17, 19, 21, 22, and 30.

Even another embodiment of the invention provides a method for evaluating cytotoxicity or carcinogenicity of an agent. A test agent is contacted with a human cell. The level of transcription of a transcript in the human cell after contacting with the agent is determined. An agent which increases the level of a transcript identified by a SAGE tag selected from the group consisting of SEQ ID NOS: 10, 15–22, 26, 27, and 30, or an agent which decreases the level of a transcript identified by a SAGE tag selected from the group consisting of SEQ ID NOS:37–67 is a potential cytotoxin or carcinogen.

Another embodiment of the invention provides a method to determine the neoplastic status or p53 status of a cell. ROS levels in a first sample of a first tissue are compared to ROS levels in a second sample of a second tissue. The first tissue is or is suspected of being neoplastic, and the second tissue is a normal human tissue. Elevated levels of ROS in the first sample indicate expression of p53, and low levels of ROS in the first sample indicate lack of expression of p53. Lack of expression of p53 is an indicator of neoplasia.

Still another embodiment of the invention provides a DNA construct for screening drugs as anti-neoplastic agents. The DNA construct comprises a reporter gene under the control of a PIG-3 promoter. The reporter gene is 3' and covalently linked to the PIG-3 promoter. The PIG-3 promoter comprises the sequence CAGCTTGCCCACCCAT-GCTC (SEQ ID NO:1).

A further embodiment of the invention provides a method of diagnosing cancer or determining p53 status in a sample suspected of being neoplastic. Cells of a test sample are treated with a DNA-damaging agent. The level of transcription of an RNA transcript in cells of the sample is compared to the level of transcription of the transcript in cells of the sample which are not subject to said treating. The transcript is identified by a tag selected from the group consisting of SEQ ID NOS:10, 15–22, 26, 27, and 30. The sample is characterized as neoplastic or as having a mutant p53 when transcription is found to be the same or lower in the treated cells than in the untreated cells.

Another embodiment of the invention provides a method of diagnosing cancer or determining p53 status in a sample suspected of being neoplastic. Cells of a test sample are treated with a DNA-damaging agent. The level of transcription of an RNA transcript in the cells is compared to the level of transcription of the transcript in cells of the sample which are not subject to said treating. The transcript is identified by a tag selected from the group consisting SEQ ID NOS:37–67. The sample is categorized as neoplastic or as having a mutant p53 when transcription is found to be the same or higher in the treated cells than in the untreated cells.

Even another embodiment of the invention provides a preparation of antibodies which specifically bind to a PIG protein having an amino acid sequence selected from the group consisting of SEQ ID NOS:81, 83, 84, 86, 87, and 88.

Still another embodiment of the invention provides a method of diagnosing cancer or determining p53 status in a sample suspected of being neoplastic. The level of a PIG protein having an amino acid sequence selected from the group consisting of SEQ ID NOS:79–88 and the amino acid sequence encoded by SEQ ID NO:72 in a first sample of a first tissue is compared to the level of the PIG protein in a second sample of a second tissue. The first tissue is suspected of being neoplastic, and the second tissue is a normal human tissue. The first and second tissue are of the same tissue type. The first sample is categorized as neoplastic or as having a mutant p53 when the level of the PIG protein is found to be the same or lower in the first sample than in the second sample.

Yet another embodiment of the invention provides a method of diagnosing cancer or determining p53 status in a sample suspected of being neoplastic. The level of a protein of Table 2 in a first sample of a first tissue is compared to the level of the protein of Table 2 in a second sample of a second tissue. The first tissue is suspected of being neoplastic, and the second tissue is a normal human tissue. The first and second tissue are of the same tissue type. The first sample is categorized as neoplastic or as having a mutant p53 when the level of the protein of Table 2 is found to be the same or higher in the first sample than in the second sample.

Even another embodiment of the invention provides a kit for evaluating toxicity or carcinogenicity of an agent. The kit comprises at least 2 antibodies which specifically bind to a PIG protein having an amino acid sequence selected from the group consisting of SEQ ID NOS:81, 83, 84, 86, 87, and 88.

Still another embodiment of the invention provides a method for evaluating cytotoxicity or carcinogenicity of an agent. A test agent is contacted with a human cell. The level of a PIG protein having an amino acid sequence selected from the group consisting of SEQ ID NOS:79–88 and the amino acid sequence encoded by SEQ ID NO:72 or of a protein of Table 2 in the human cell is determined after contacting with the agent. An agent which increases the level of the PIG protein or an agent which decreases the level of the protein of Table 2 is identified as a potential cytotoxin or carcinogen.

A further embodiment of the invention provides a method of diagnosing cancer or determining p53 status in a sample suspected of being neoplastic. Cells of a test sample are treated with a DNA-damaging agent. The level of a PIG protein having an amino acid sequence selected from the group consisting of SEQ ID NOS:79–88 and the amino acid sequence encoded by SEQ ID NO:72 in cells of the sample is compared to the level of the PIG protein in cells of the sample which are not subject to said treating. The sample is categorized as neoplastic or as having a mutant p53 when the level of the PIG protein is found to be the same or lower in the treated cells than in the untreated cells.

Even another embodiment of the invention provides a method of diagnosing cancer or determining p53 status in a sample suspected of being neoplastic. Cells of a test sample are treated with a DNA-damaging agent. The level of a protein of Table 2 in cells of the sample is compared to the level of the protein of Table 2 in cells of the sample which are not subject to said treating. The sample is categorized as neoplastic or as having a mutant p53 when the level of the protein of Table 2 is found to be the same or higher in the treated cells than in the untreated cells.

These and other embodiments of the invention provide the art with tools for assessing p53 status in cells, which can provide diagnostic and prognostic information useful in the evaluation of patients and the management of cancer.

BRIEF DESCRIPTION OF THE DRAWINGS

FIG. 3. Sequences of selected genes identified through SAGE. In each case, the indicated gene is compared to the homologue from the non-human species that revealed a clue to its possible function. The amino acid sequences were aligned using Macaw Version 2.0.3, and the most significant similarities are indicated by shading. With the exception of PIG6, the cloned human sequences appeared to be full length with respect to the coding region. Accession numbers are provided in Table 1.

FIG. 3A, human PIG3 (SEQ ID NO:87) and rat micGST (SEQ ID NO:88).

FIG. 3B, human PIG3 (SEQ ID NO:81) and Vigna TED2 (SEQ ID NO:89).

FIG. 3C, human PIG8 (SEQ ID NO:90) and C. elegans f37c12 (SEQ ID NO:91). FIG. 3D, human PIG6 (SEQ ID NO:92) and Drosophila PUT1 (SEQ ID NO:93).

FIG. 4. Oxidative stress and mitochondrial damage in p53-mediated apoptosis.

DETAILED DESCRIPTION

Figure 1A:
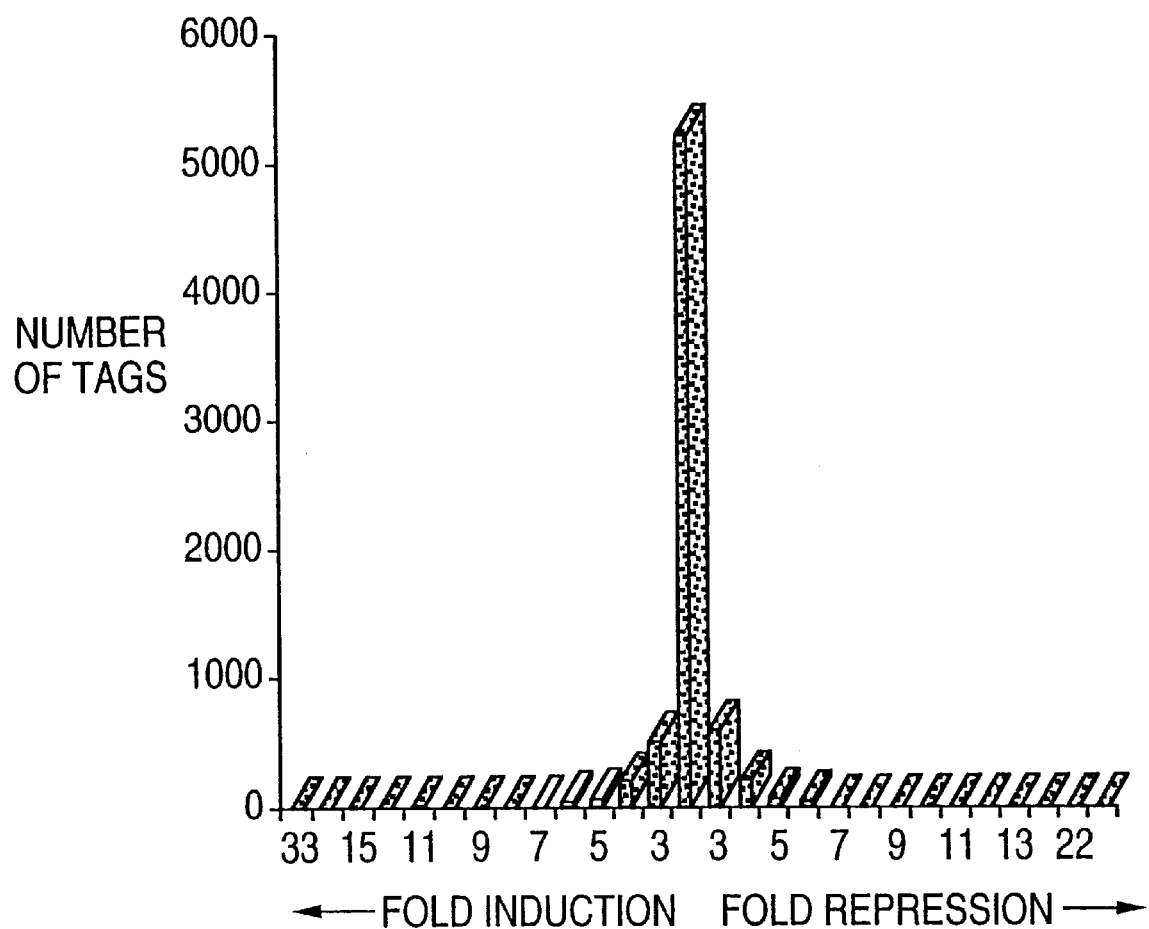
FIG. 1A. Summary of SAGE data. For each of 7,202 different transcripts identified, the ratio of their abundances in two libraries is plotted. The y-axis indicates the number of tags expressed at the ratio indicated on the x-axis. Bars representing tags exhibiting less than 5-fold differences in expression are shown in green, and those induced or repressed more than 8-fold are shown in blue and red, respectively.

The most well-documented biochemical property of p53 is its ability to transcriptionally activate genes. Of 7,202 transcripts induced by p53 expression prior to the onset of apoptosis, only 14 (0.19%) are found at markedly higher levels in p53-expressing cells than in control cells. The genes encoding these transcripts are termed PIGS (p53-induced genes). Many of these genes are predicted to encode proteins which could generate or respond to oxidative stress, including one that is implicated in apoptosis within plant meristems. Thus, p53 may result in apoptosis through a three-step process: (i) the transcriptional induction of specific redox-related genes; (ii) the formation of reactive oxygen species (ROS); and (iii) the oxidative degradation of mitochondrial components, rapidly leading to in cell death.

Using the SAGE tags disclosed in Tables 1 and 2, transcripts can be evaluated for enhanced or reduced expression, respectively. A SAGE tag is a short sequence tag, preferably 10 or 11 base pairs, which is generated from defined positions within each mRNA molecule. Expression patterns are deduced from the abundance of individual tags. The altered expression can provide an indication of the status of the p53 genes in the cells, which themselves reflect the neoplastic status of cells. While the presence of wild-type p53 is not determinative of normalcy, the presence of mutant p53 is an indication of neoplasia.

The tags which are shown in Table 1 identify transcripts which are enhanced by p53; the tags of Table 2 identify transcripts which are decreased by p53. Wild-type p53 is required for these modulations. Thus failure to so-modulate is an indication of mutant p53 in the cell. Similarly, DNA-damaging agents which cause apoptosis do so via wild-type p53. In the absence of wild-type p53 these agents cannot induce transcription of the Table 1 tag-identified transcripts nor can they decrease transcription of the Table 2 tag-identified transcripts. Thus, analysis of the status of these transcripts can provide an indication of the presence or absence of wild-type p53.

Cells can be compared from suspect tissues to normal tissues. Similarly, a suspect or test tissue sample can be treated with a DNA-damaging agent and the response of the cells in the tissue assessed. The response assessed is the induction or reduction in the transcripts identified by the tags. Tags "identify" transcripts by hybridization to them. This hybridization can be determined using any method of measuring transcription, including but not limited to Northern blots, quantitative RT PCR, etc. Conditions for optimizing hybridization signals and minimizing background are known in the art and can be selected by the skilled artisan. Preferably an assay is done with at least two, five, or ten of the transcripts which are known to be modulated by p53. More preferably one or more of the tags used is selected from SEQ ID NOS:15–17, 19, 21, 22, or 30. Suitable DNA-damaging agents include adriamycin, mitomycin, alkylating agents, and γ- and UV-radiation.

Isolated and purified nucleic acid molecules which include a SAGE tag particularly SEQ ID NOS:15–17, 19, 21, 22, or 30, are also provided. These can be made using the SAGE tags to isolate a full length RNA, which is then reverse transcribed using reverse transcriptase to form cDNA. Alternatively the SAGE tags can be used to identify clones from cDNA libraries using hybridization. The SAGE tags can also be used as primers to generate PCR products which contain the SAGE tags. Any such method known in the art can be used. Isolated and purified nucleic acid molecules are free of other nucleic acid molecules with which they are found in cells. Preferably they are also free of the genes to which they are adjacent in the chromosome.

Nucleotide probes are typically less than full length genes and can be labeled so that they can be used in hybridization experiments. Such probes are typically at least 12 contiguous nucleotides in length. Probes of the invention can comprise a SAGE tag of Tables 1 and 2, particularly SEQ ID NOS:15–17, 19, 21, 22, or 30, or can comprise a different portion of a transcript or cDNA molecule identified by such SAGE tags.

Kits can be formulated for evaluating toxicity or carcinogenicity of test agents. The kits comprise at least 2, 3, 4, 5, 6, 7, 8, 9, or 10 probes which are complementary to the transcripts identified by the SAGE tags of Table 1 and 2. Just as DNA-damaging agents induce apoptosis via p53, which can be measured by measuring the induction or repression of expression of specific transcripts, so can other as yet unknown agents. Such agents which cause DNA damage are likely to be toxic or carcinogenic. Thus, human cells can be contacted with a test agent, and the levels of one or more transcripts identified by a SAGE tag in Table 1 or 2 can be measured. If the agent causes the modulation which is caused by the introduction of wild-type p53 or the modulation which is caused by DNA-damaging agents in wild-type p53-containing cells, then the agent is a suspected carcinogen or toxic agent.

Reactive Oxygen Species PROS) production can also be used as an indicator of p53 status and hence neoplasia.

Levels of ROS can be determined and compared between cells of a tissue which is suspected of being neoplastic and normal cells. Elevated levels of ROS indicate expression of p53, and low levels indicate lack of p53 expression. These levels can be measured after contacting the cells with an agent which induces DNA damage. Alternatively a test sample can be tested before and after treatment with DNA damaging agents. The ability to induce ROS indicates a wild-type p53. Any method for measuring ROS can be used, including but not limited to carboxymethyl dichlorofluorescein diacetate and flow cytometry, nonylacridine orange as a probe for cardiolipin, lucigenin chemiluminescence, and intracellular glutathione.

DNA constructs which contain a reporter gene under the transcriptional control of a PIG promoter can be used to test agents for the ability to induce apoptosis. Such agents have potential use as anti-neoplastic agents. One such construct contains the PIG-3 promoter which contains the p53-binding site CAGCTTGCCCACCCATGCTC (SEQ ID NO:1). Other PIG promoters can be used similarly.

PIG-specific antibodies can be used in assays to determine the status of the p53 gene in cells similar to those described above employing SAGE tags. Proteins or polypeptides encoded by PIGs 1–7 and 9–12 (PIG proteins) can be purified by any method known in the art or produced by recombinant DNA methods or by synthetic chemical methods and used as immunogens, to obtain a preparation of antibodies which specifically bind to a PIG protein, preferably to PIG 3, 6, 7, 10, 11, or 12. The antibodies can be used to detect wild-type PIG proteins in human tissue and fractions thereof.

Preparations of polyclonal or monoclonal PIG antibodies can be made using standard methods known in the art. The antibodies specifically bind to epitopes present in PIG proteins. Preferably, the PIG epitopes are not present in other human proteins. Typically, at least 6, 8, 10, or 12 contiguous amino acids are required to form an epitope. However, epitopes which involve non-contiguous amino acids may require more, e.g., at least 15, 25, or 50 amino acids. Antibodies which specifically bind to PIG proteins provide a detection signal at least 5-, 10-, or 20-fold higher than a detection signal provided with other proteins when used in Western blots or other immunochemical assays. Preferably, antibodies which specifically bind PIG proteins do not detect other proteins in immunochemical assays and can immunoprecipitate PIG proteins from solution.

Antibodies which specifically bind to PIG proteins, particularly to PIG 3, 6, 7, 10, 11, or 12, can be purified by methods well known in the art. Preferably, the antibodies are affinity purified, by passing antiserum over a column to which a PIG protein or polypeptide is bound. The bound antibodies can then be eluted from the column, for example, using a buffer with a high salt concentration.

As disclosed above, wild-type p53 is required to modulate the level of transcripts identified in Tables 1 and 2, and the presence of mutant p53 is an indication of neoplasia. For example, wild-type p53 increases transcription of genes shown in Table 1 and decreases transcription of genes shown in Table 2. The status of the p53 gene in a tissue suspected of being neoplastic can be determined by comparing the levels of one or more of the products of genes whose transcription is modulated by wild-type p53 in the suspect tissue with the level of a PIG protein in a tissue which is normal.

Such comparisons can be made by any methods known in the art. Preferably, antibodies which specifically bind to the protein products of the modulated genes are used, for example in radioimmunoassays or immunocytochemical methods, as is known in the art. Antibodies which specifically bind to the proteins of Table 2 can be used to measure the levels of the proteins of Table 2. Antibodies which specifically bind to PIGs 1–7 and 9–12, particularly those which specifically bind to PIG 3, 6, 7, 10, 11, and 12, can be used to measure the levels of PIG proteins.

The same or a lower level of a PIG protein in the suspect tissue indicates the presence of mutant p53. Similarly, the same or a higher level of a protein of Table 2 in the suspect tissue indicates the presence of mutant p53. The levels of two, 3, 4, 5, 6, 7, 8, 9, or 10 or more proteins can be compared. Detection of binding of PIG-specific antibodies to PIG proteins, or of antibodies which specifically bind to the proteins of Table 2, can also be used to determine if a suspect tissue contains a wild-type or mutant p53 gene after treatment with DNA-damaging agents.

Antibodies of the invention which specifically bind to PIG 3, 6, 7, 10, 11, or 12 can be provided in kits, for evaluating cytotoxicity or carcinogenicity of test agents, as described above. A kit can contain one, 2, 3, 4, 5, or 6 of the antibodies of the invention.

The above disclosure generally describes the present invention. A more complete understanding can be obtained by reference to the following specific examples which are provided herein for purposes of illustration only, and are not intended to limit the scope of the invention. The following methods were used in the examples reported below.

Methods

Cells and RNA. All cell lines used in this study were obtained from the American Type Culture Collection and were cultured in McCoy's medium supplemented with 10% fetal bovine serum (FBS). Cells were infected with recombinant adenoviruses containing either the p53 gene or the β-galactosidase gene (26) at a multiplicity of infection of 10–100. RNA was purified from cells at various times after infection using the MessageMaker Kit (Gibco/BRL). Northern blot analysis was performed as described (26).

SAGE. SAGE was performed as previously described (3, 27). Briefly, polyadenylated RNA was converted to double-stranded cDNA with a BRL synthesis kit using the manufacturer's protocol with the inclusion of primer biotin-5'-T18-3'. The cDNA was cleaved with NlaIII, and the 3'-terminal cDNA fragments were bound to streptavidin-coated magnetic beads (Dynal). After ligation of oligonucleotides containing recognition sites for BsmFI, the linkered-cDNA was released from the beads by digestion with BsmFI. The released tags were ligated to one another, concatemerized, and cloned into the Sph I site of pZero 21.0 (Invitrogen). Colonies were screened with PCR using M13 forward and M13 reverse primers. PCR products containing inserts of greater than 300 bp (>20 tags) were sequenced with the TaqFS DyePrimer kit and analyzed using a 377 ABI automated sequencer Perkin Elmer).

Statistical analysis. 53,022 and 51,853 tags were identified from DLD-1 cells infected with Ad-p53 and Ad-lacZ, respectively. The two libraries were compared using the SAGE program group (3). Corrections for tags containing linker sequences and other potential artifacts were made as described previously (27). Of 104,875 total tags identified, 3,181 were excluded from analysis on this basis. Monte Carlo simulations revealed that the computational analyses had a >99% probability of detecting a transcript expressed at an abundance of 0.00005 in either RNA sample.

cDNA clones. Cellular mRNA from Ad-p53-infected cells was used to prepare cDNA as described for the SAGE libraries, except that the 3' primer contained an additional M13 forward sequence between the olio-DT tract and the biotinylated 5' residue. To determine the sequence of the transcript from which an individual tag was derived, this cDNA was used as a template for PCR, employing an M13 forward primer and a primer containing the tag sequence. In other cases, mRNA from Ad-p53-infected cells was used to construct a cDNA library in the ZAP Express vector (Stratagene) and the library was screened by hybridization with oligonucleotides corresponding to tags, as described (3). Of 14 tags identified by SAGE as differentially expressed in p53-expressing cells, 8 corresponding genes could be identified simply by searching public databases, particularly those including expressed sequence tags. In 5 cases, one of the two strategies described above was used to obtain the corresponding PIG. In one of the 14 cases PIG13), no cDNA clone could be recovered corresponding to the tag sequence.

Figure 2A:
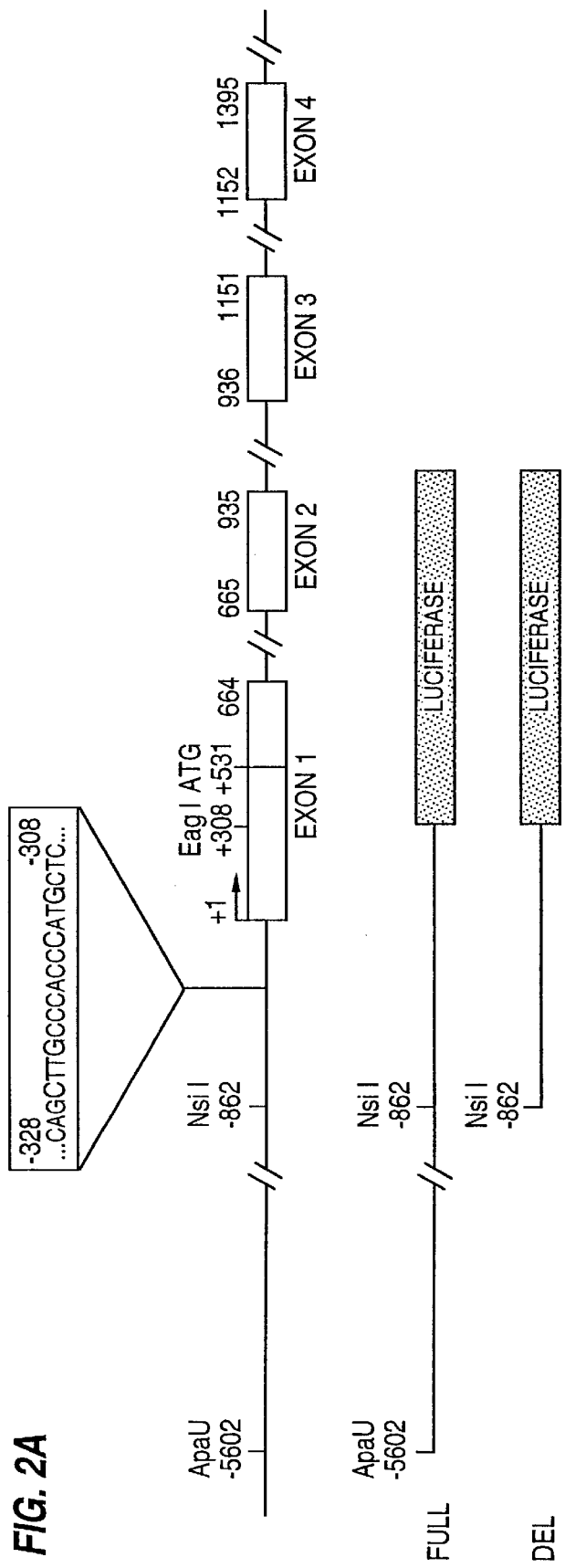
FIG. 2A. Schematic of PIG3 gene, illustrating intron-exon structure and promoter region. Numbers refer to nucleotides relative to the 5' end of the cDNA. The fragments used for the luciferase constructs had their distal ends at the Eag I site within exon 1 and their 5' ends at either the Apa LI or Nsi I sites (FULL and DEL, respectively). The 53-binding site located at nucleotides 328–308 is indicated, with the upper case letters corresponding to the highly conserved residues that were altered in one of the oligonucleotides used for immunoprecipitation.

Analysis of PIG3 genomic structure. An arrayed BAC library (Research Genetics) was screened by PCR using the following primers derived from the 5' end of the PIG3 gene: 5'-GGC-CAG-GAG-TAA-GTA-ACT-3' (SEQ ID NO:2) and 5'-GCC-CTG-GTC-TGC-CGC-GGA-3' (SEQ ID NO:3). Eco RI fragments encompassing the PIG3 coding sequences were subcloned into pBR322 and partially sequenced to determine the intron-exon borders. A 6.1 kb Apa LI fragment whose 3' end was at a Eag I site 308 bp downstream of the transcription start site was then cloned into a promoterless luciferase reporter vector (FIG. 2A). This fragment was completely sequenced by primer walking. Subclones were then generated by restriction endonuclease digestion. Luciferase activity was determined after co-transfection with expression vectors encoding wt or H175R mutant p53. For in vitro p53 binding experiments, oligonucleotides containing two copies of the predicted p53-binding site (FIG. 2A) were subcloned into a modified pBR322 vector, excised as a ~260 bp restriction fragment, and end-labeled. Immunochemical assays were performed as described previously (28).

Flow cytometry and other assays. Cells were collected with the aid of trypsin and incubated with CM-H2DCF-DA or NAO (Molecular Probes, Eugene, Oreg.) at concentrations of 10 and 0.4 $\mu$M, respectively, for 20 minutes at 37° C. prior to analysis by flow cytometry (14,15). To determine the fraction of apoptotic cells after various treatments, cells were stained with the DNA-binding dye H33258 and evaluated by fluorescence microscopy or flow cytometry as described (1). Superoxide production was assessed with lucigenin (29). In brief, 4–5×10$^6$ cells were collected with rubber policeman and resuspended in 1 ml of Earle's Balanced Salt Solution (Gibco BRL 14015-069, Life Technologies). Dark-adapted lucigenin (bis-N-methulacridinium nitrate, Sigma M8010) was added to the samples to a final concentration of 20 $\mu$M. Light emission was detected using a Berthold LB 9505C luminometer for 60 minutes at 37° C. Glutathione concentrations were measured using an assay kit purchased from Oxford Biomedical Res. Inc. according to the manufacturer's instructions. Caspase activation was assessed by cleavage of PARP (polyADP-ribose polymerase). Lysates from cells infected with Ad-p53 were Western blotted with an anti-PARP antibody, and the cleavage fragments were quantitated by densitometry (4).

EXAMPLE 1

To evaluate the patterns of gene expression following p53 expression, we employed SAGE, a technique which allows the quantitative evaluation of cellular mRNA populations (3). In brief, the method revolves around short sequence "tags" (11 bp), generated from defined positions within each mRNA molecule. Expression patterns are deduced from the abundance of individual tags. To induce apoptosis, the colorectal cancer line DLD-1, containing an inactive endogenous p53 gene, was infected with a replication defective adenovirus encoding p53 (Ad-p53). As previously shown, DLD-1 cells are among the ~50% of CRC lines that undergo apoptosis in response to p53 (4). RNA was purified from cells 16 hours after infection, at least 8 hours before the onset of morphological signs of apoptosis.

A total of 101,694 tags were analyzed, approximately half from cells infected with Ad-p53 and half from cells infected with a control virus (Ad-lacZ) encoding $\beta$-galactosidase. These tags corresponded to 7,202 different transcripts. Comparison of the two SAGE libraries indicated a remarkable similarity in expression profiles (FIG. 1A). Of the 7,202 transcripts detected, only 14 (0.19%) were expressed at levels more than 10-fold greater in p53-expressing than in control cells; conversely, only 20 transcripts were expressed at levels less than 10-fold lower in the p53-expressing cells.

As previous data indicated p53-mediated transcriptional activation as the likely basis of p53 action (5), we concentrated on the 14 tags appearing at higher levels in the p53-expressing cells. The mRNA transcripts corresponding to 13 of these tags were successfully identified (Table 1). In each case, the induction was confirmed by Northern blot analysis (examples in FIG. 1B). Only two of these genes (called PIGs, for p53-induced genes) had been implicated as targets of p53-transcriptional activation (1, 2, 5, 6) and seven had not previously been described at all. Other genes previously implicated in p53-mediated responses were induced to lower levels (e.g., MDM2, thrombospondin) or not at all (e.g., bax and cyclin G1) in the human CRC cells studied here (4).

EXAMPLE 2

Figure 1B:
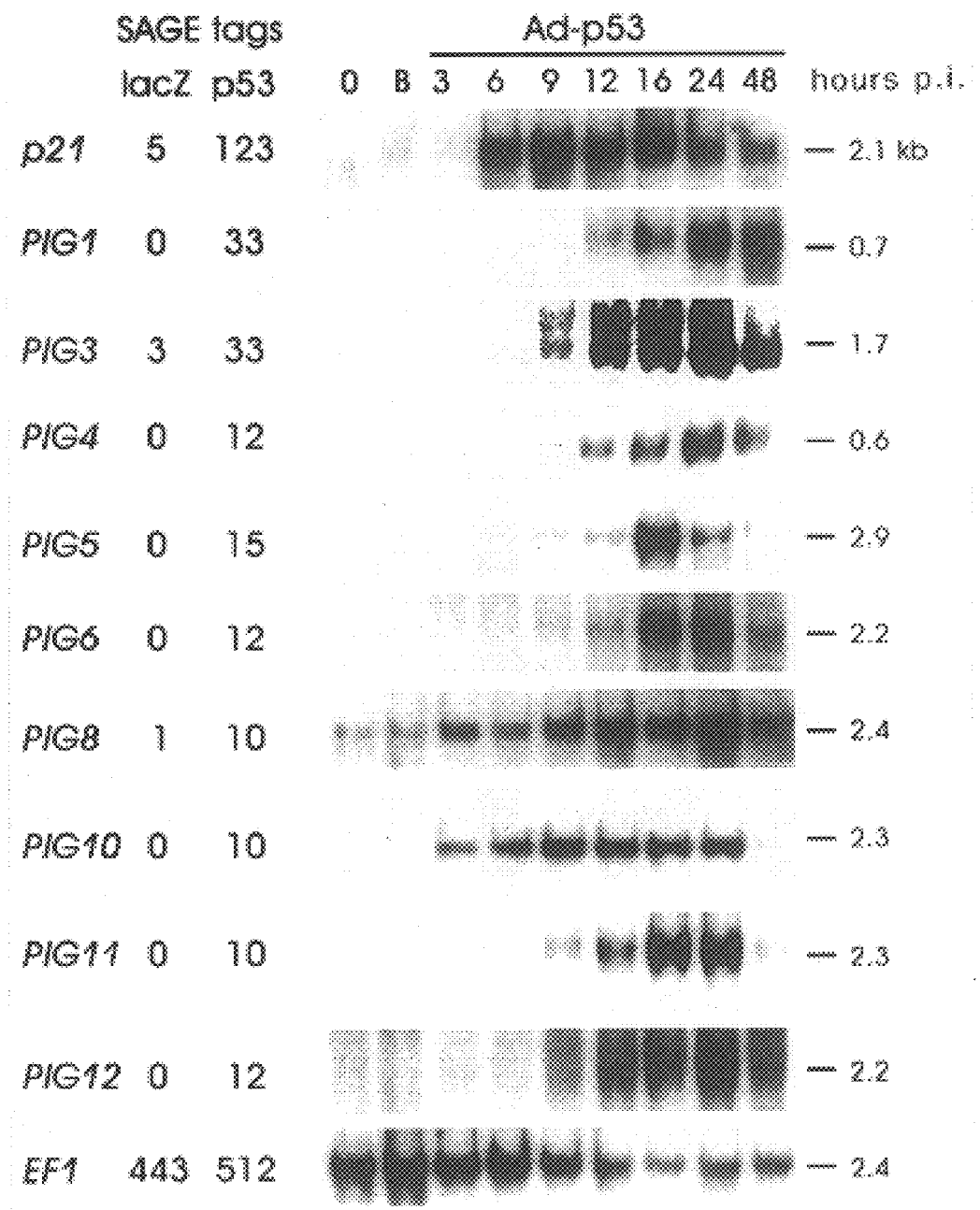
FIG. 1B. Northern blot analysis after Ad-p53 infection. Representative Northern blots are shown for several transcripts identified by SAGE to be expressed at higher levels in p53-expressing cells at the indicated times post infection. Uninfected cells (column marked "0") and cells infected with Ad-lacZ for 48 hrs (column marked "B") were included for comparison. EF1 is a control transcript expressed at relatively equal levels in cells 16 hours after infection with Ad-p53 and Ad-acZ. The SAGE tag abundances (16 hours after infection) are included at the right.

PIGs were induced at relatively short times after p53 expression, at least 12 hours prior to any morphological or biochemical signs of apoptosis FIG. 1B). This time course suggested that PIGs were directly induced by the transcriptional activation properties of p53. To formally test this conjecture in a representative case, we evaluated the genomic structure and sequence of PIG3. By screening a bacterial artificial chromosome (SAC) library, a genomic clone was identified that contained all PIG3 coding sequences. The gene was localized to chromosome 2p (see Methods), and the intron-exon structure and sequence of the promoter region were determined.

A 6.1 kb ApaLI fragment of genomic DNA containing the presumptive promoter was then cloned upstream of a luciferase reporter gene (FIG. 2A). The resulting construct was transfected into three different human cell lines together with wild type (wt) or mutant p53.

Figure 2B:
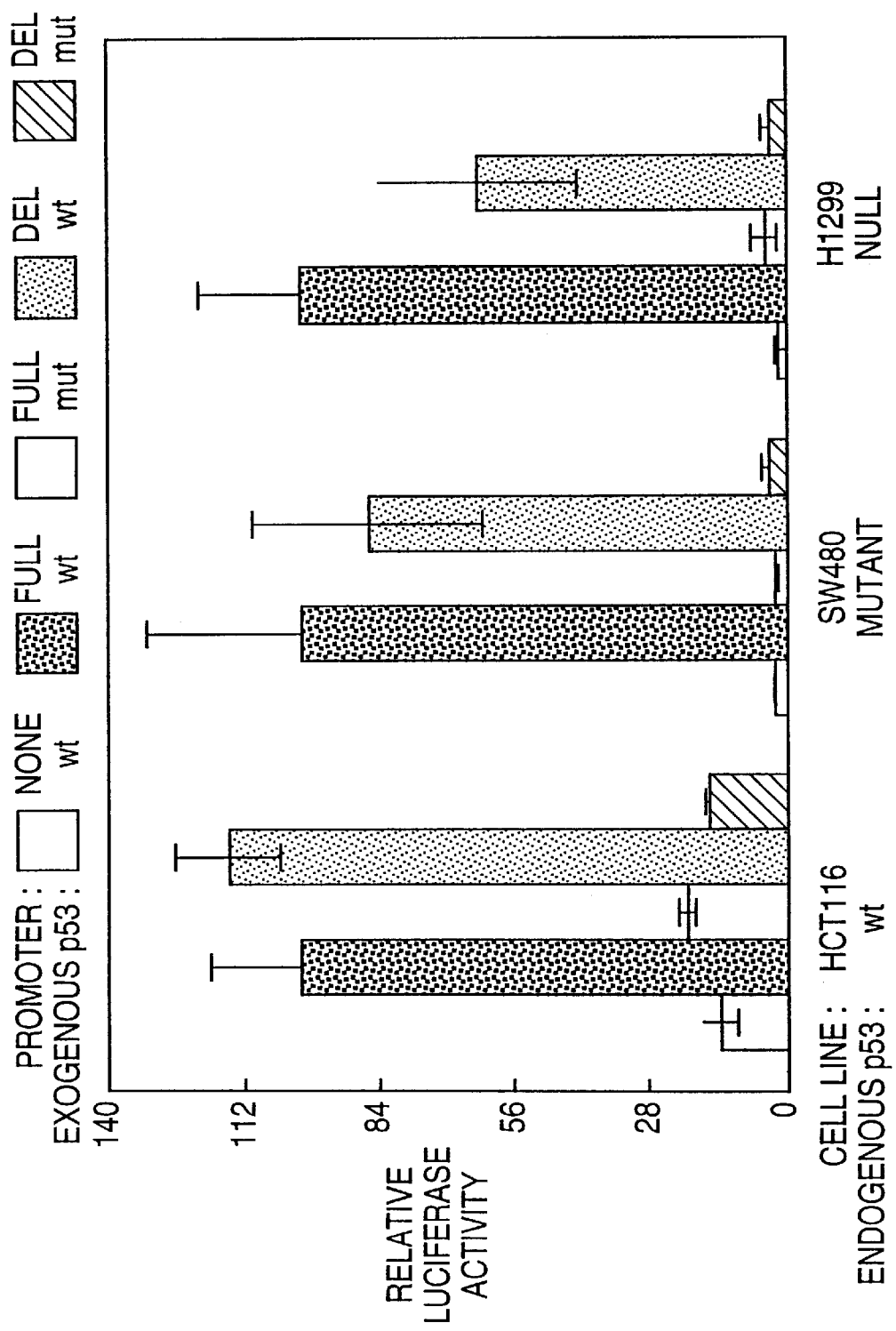
FIG. 2B. p53-induction of the PIG3 promoter. Fragments encompassing 5.6 or 0.7 kb (FULL and DEL, respectively) of the PIG3 gene promoter were cloned upstream of a luciferase reporter and transfected into the indicated cell types in the presence of wt and mutant p53 expression vectors. The levels of luciferase activity were determined in cell lysates 24 hours after transfection.
Figure 2C:
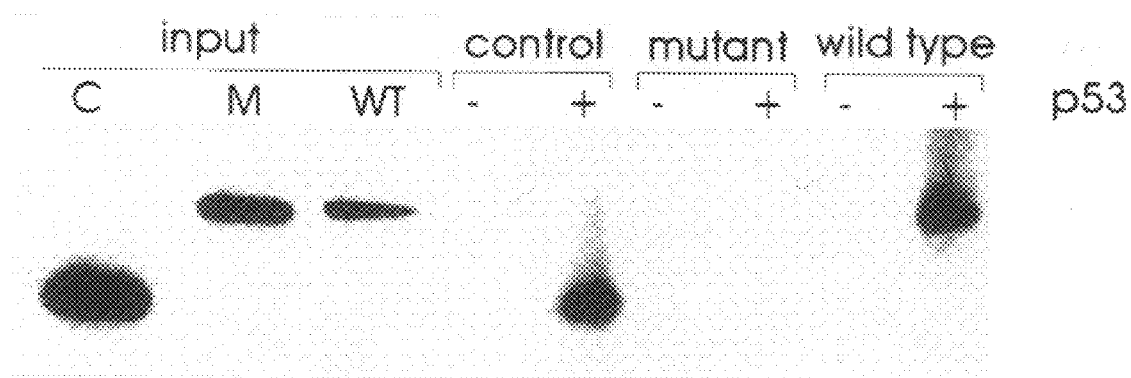
FIG. 2C. In vitro binding assay with end-labeled fragments containing wild type (WT) and mutant (M) p53 binding sites. A fragment containing thirteen copies of a p53 binding site from the WAF1 promoter region 3026 was used as a control (C). The "input" lanes contained 0.5% of the amount of fragment used in the binding assays.

As shown in FIG. 2B, wt p53 induced substantial activity through the PIG3 promoter in all three lines. Mutant p53 had no transcriptional activation capacity. Analysis of a truncated promoter showed that the p53-responsive elements lay within a fragment containing only 862 bp of sequence upstream of the PIG3 transcription start site (FIG. 2A). Determination of the sequence of this 6.1 kb Apa L1 fragment revealed a single 20 bp sequence predicted to bind p53, located at 308 nt upstream of the transcription start site p53. A DNA fragment containing two copies of this sequence, but not a derivative of this fragment altered at critical residues, was found to bind strongly to p53 in vitro FIG. 2C).

EXAMPLE 3

As a further test of the p53-dependency of PIG3 induction, we determined whether PIG3 could be induced by endogenous p53 rather than through the exogenous Ad-p53 source. Six CRC cancer cell lines were each treated with adriamycin, a DNA-damaging and apoptotic-inducing agent known to increase endogenous p53 levels. PIG3, like p21, was found to be strongly induced in the three lines with wild-type p53 genes, but not in the three lines with mutant p53 genes.

EXAMPLE 4

The sequences of the PIGs provided important clues to their potential functions (Table 1). In particular, several were predicted to encode proteins with activities related to the redox status of cells. PIG12 is a novel member of the microsomal glutathione transferase family of genes (FIG. 3A). PIG8 is the human homologue of a mouse gene (Ei24) whose expression is induced in a p53-dependent manner by etoposide, a quinone known to generate reactive oxygen species (ROS) (6) (FIG. 3C). PIG6 is a homolog of proline oxidoreductase (FIG. 3D), a mitochondrial enzyme that catalyzes the first step in the conversion of proline to glutamate (7). Glutamate is one of the three amino acids required for formation of glutathione, a major regulator of cellular redox status. The p21 gene, which can also be considered a PIG, can be induced by ROS, independently of p53 (8). PIG4 encodes a serum amyloid protein that can be induced by oxidative stress (9). PIG1 belongs to the galectin family, members of which can stimulate superoxide production (10). PIG7 has been shown to be induced by TNF-β, a known inducer of oxidative stress. PIG3 is a novel gene that is highly related to TED2, a plant NADPH oxidoreductase (11) (FIG. 3B). Interestingly, TED2 is one of the few genes implicated in the apoptotic process necessary for the formation of plant meristems (11). The closest relative of PIG3 in mammals is an NADPH-quinone oxidoreductase which has been shown to be a potent generator of ROS (12).

Figure 4A:
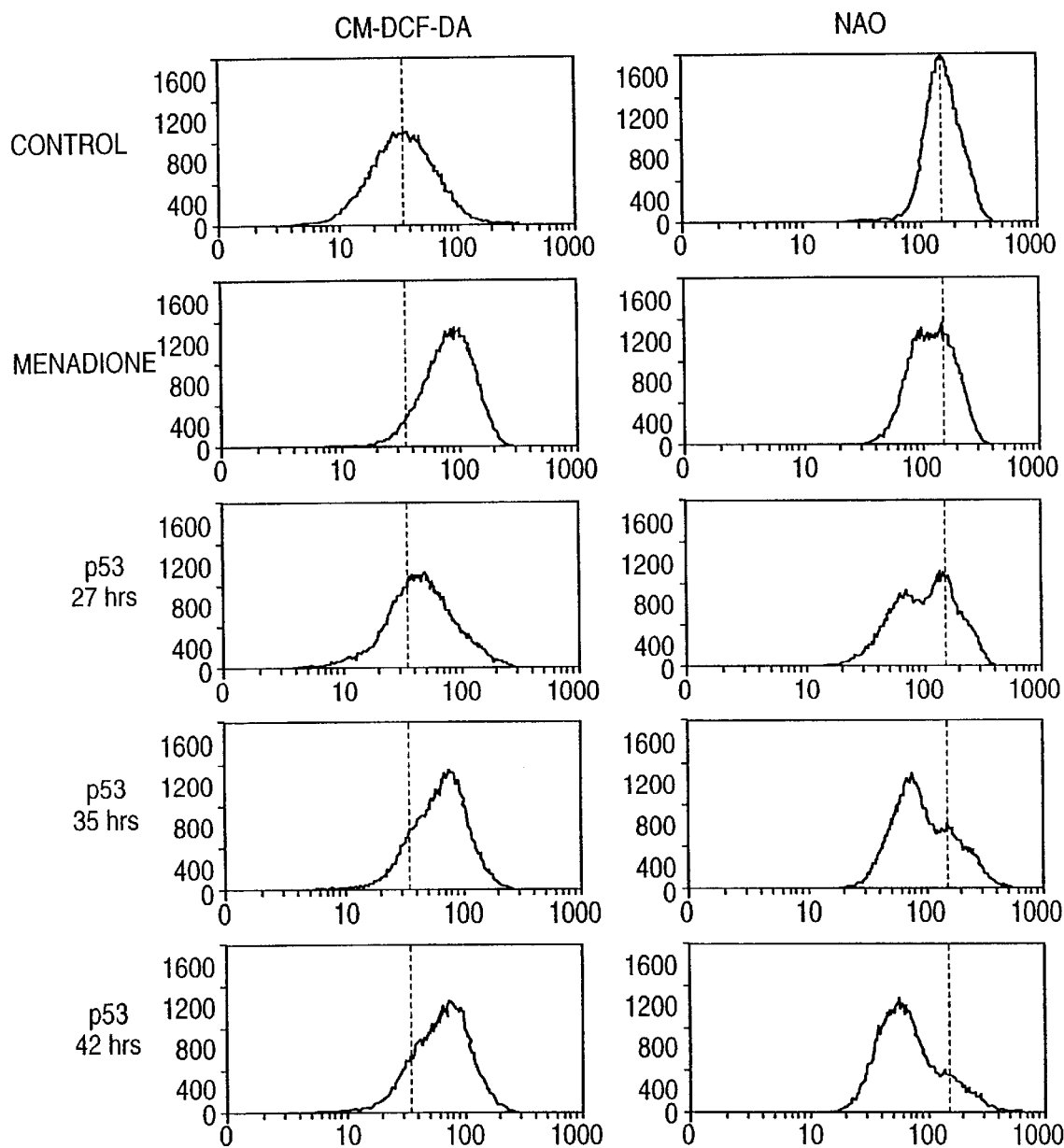
FIG. 4A. DLD-1 cells were infected with Ad-p53 or control (Ad-lacZ) viruses and harvested after 27, 35, or 42 hours. Cells were incubated with CM-DCF-DA, a probe of ROS, or NAO, a probe of the mitochondrial membrane cardiolipin, and analyzed by flow cytometry. The mean fluorescence of the control cells is indicated by vertical lines in each box. The pro-oxidant drug menadione was used as a positive control to induce oxidative stress. An increase in ROS and a decrease in cardiolipin concentration could be clearly observed by cytometry at 27 hours and increased as the p53-expressing cells entered apoptosis.

Previous studies have shown that ROS are powerful inducers of apoptosis (13). The SAGE-based characterization of p53-induced genes suggested that p53 might induce apoptosis by stimulating the production of ROS. To test this hypothesis, the production of ROS was measured in p53-expressing cells using carboxy-methyl dichlorofluorescein (DCF-diacetate (CM-DCF-DA) and flow cytometry (14). This analysis showed that ROS were induced following Ad-p53 infection and that ROS continued to increase as apoptosis progressed (FIG. 4A). The magnitude of the increase in ROS, as assessed by DCF fluorescence, was similar in p53-expressing cells to that observed in cells treated with the powerful oxidant menadione (FIG. 4A). No change in DCF fluorescence was observed following infection with a control adenovirus (FIG. 4A).

As an assay for the functional consequences of ROS production, we examined the cellular content of cardiolipin, a major component of the mitochondrial membrane which is especially sensitive to cellular oxidation (15). Using nonyl-acridine orange (NAO) as a probe, cardiolipin was found to decrease soon after p53-induced ROS was detected (FIG. 4A), demonstrating significant injury to a major mitochondrial component.

EXAMPLE 5

To determine the specificity of PIG expression for the p53-dependent apoptotic process, we performed experiments with other inducers of ROS or apoptosis. We found that PIGs were not expressed simply as a result of ROS production, as none were induced following treatment with menadione and only p21 was induced by hydrogen peroxide in DLD-1 cells. Similarly, the specificity of PIG induction for p53-dependent apoptosis was confirmed by the demonstration that other inducers of apoptosis (indomethacin or ceramide) did not result in the expression of any PIG, despite extensive cell death.

EXAMPLE 6

Figure 4B:
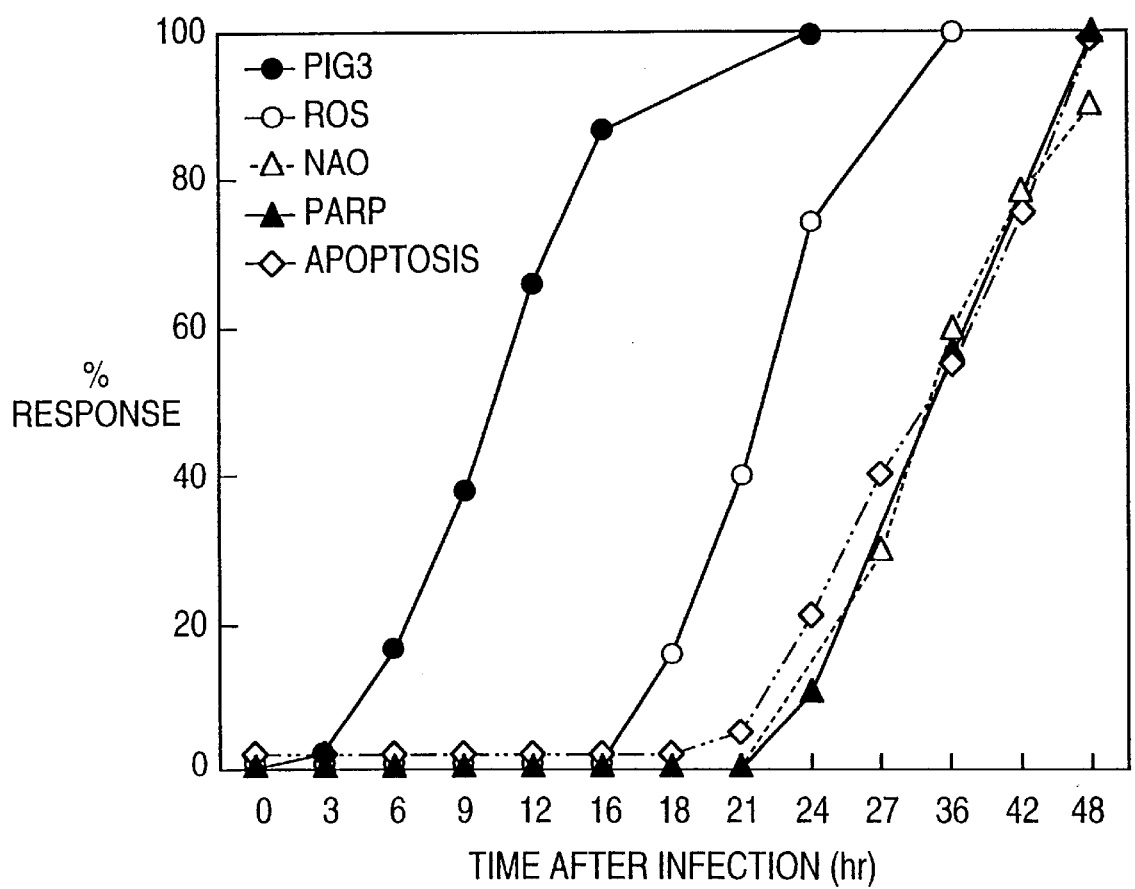
FIG. 4B. Time course of apoptosis-related events following p53 expression. Cells were infected with Ad-p53 at 0 hours and PIG3 expression (●) was quantitated by densitometry of Northern blots. ROS production (○) was assessed with lucigenin; glutathione depletion exhibited a similar time course (not shown). Cardiolipin concentration (Δ) was assessed with nonyl-acridine orange staining. Caspase activation (▲) was assessed by cleavage of PARP, and chromatin condensation/fragmentation (◇) was assessed by staining with DAPI.

To clarify the relationship between p53 expression, PIG activation, ROS production, and apoptosis, we carried out more detailed time course experiments. PIG induction began within six hours after Ad-53 infection (FIG. 1B and FIG. 4B), while intracellular ROS production, as assessed with lucigenin chemiluminescence, could first be observed at 18 hours (FIG. 4B). This ROS production led to oxidative stress, as evidenced by a 48+/−12% decrease in intracellular glutathione concentration at 21 hours. Mitochondrial lipid degradation (NAO) was not observed until three to six hours after the onset of a measurable ROS increase and was accompanied by morphologic (chromatin condensation and fragmentation) and biochemical (caspase-mediated degradation of PARP) signs of apoptosis (FIG. 4B). These observations are consistent with previous studies showing that mitochondrial damage is rapidly followed by classic signs of programmed cell death (13).

The time courses illustrated in FIG. 4B suggest a cascade wherein p53 transcriptionally induces redox-controlling genes resulting in the production of ROS, in turn leading to oxidative damage to mitochondria and apoptosis. To determine whether these steps were causally associated, we inhibited each step with specific pharmacologic agents and determined the effect of this inhibition on other components of the pathway.

First, cells were treated with the transcriptional inhibitor 5,6-dichlorobenimidizole riboside (DRB) at 8 hours following Ad-p53 infection (16). Though p53 expression was already near maximal at this time, DRB was found to block apoptosis at 24 hours by 83+/−3% as well as to inhibit the expression of PIGs. The translational inhibitor cycloheximide, when given up to 8 hours following Ad-p53 infection, was found to similarly block apoptosis (by 79% at 24 hours). Thus both transcription and translation were required for p53-induced apoptosis in CRC cells, as observed in some other systems (2, 5) and as expected for classic programmed cell death (2, 5).

Second, p53-expressing cells were treated with pyrrolidine dithiocarbamate (PDTC), an anti-oxidant which has been shown to block ROS-associated apoptosis (17). PDTC was indeed able to block the apoptosis elicited by p53. However, PDTC inhibits many enzymes, and its specificity is questionable (17). We therefore treated cells with diphenyleneiodonium chloride (DPI), a specific inhibitor of flavin-dependent oxidoreductases which has been used to block production of ROS in a variety of systems (18). Cells were treated with DPI 12 hours after Ad-p53 infection, when PIG production was already underway. PIG3 expression, apoptosis, and ROS production were measured 12 hours later. DPI (25 μM) did not inhibit PIG3 production but did inhibit ROS production by 71–85% and inhibited apoptosis by 73–77% in three independent experiments (FIG. 4D).

Finally, we treated cells with bongkrekic acid (BA), a specific inhibitor of mitochondrial ATP translocase which can block the mitochondrial permeability transition pore opening thought to be required for ROS-dependent forms of apoptosis (13). When cells were treated 12 hours after Ad-p53 infection, BA was found to inhibit neither PIG3 expression nor ROS production, but inhibited subsequent apoptosis by 86–93% (FIG. 4D). BA was non-toxic at the dose used (100 $\mu$M). While BA inhibited the p53-apoptotic process dependent on ROS production, it had no effect on the p53-mediated growth arrest dependent on p21 as assessed by flow cytometry.

The gene expression profile, time courses, and pharmacologic inhibition studies reported above strongly support a three step model underlying p53's induction of apoptosis. We propose that p53 transcriptionally activates a specific subset of genes, including oxidoreductases, long before any morphological or biochemical evidence of cell death (Table 1 and FIG. 4B). The proteins encoded by these genes then collectively increase the content of ROS, which in turn damage mitochondria. Leakage of calcium and proteinaceous components from damaged mitochondria then stimulate the caspases that are ubiquitously activated during the apoptotic process. (19–22).

Data from several experimental systems are consistent with this model. For example, apoptosis induced by irradiation, which is dependent on p53 in certain cell types, has been suggested to proceed through a process involving ROS and mitochondrial damage (23). Additionally, an SV40 large T antigen mutant, which binds p53 only at the permissive temperature, was shown to induce apoptosis at the non-permissive temperature through a ROS-related mechanism (24). More recently, it was shown that p53-induced apoptosis in smooth muscle cells is ROS-dependent (25). Though the basis for ROS production and the involvement of mitochondria were not investigated in these previous studies, they suggest that the events we observed in CRC cells are unlikely to be cell-type or species specific and may often underlie p53-associated apoptotic processes. The fact that one of the PIGs is highly related to Ted2, an oxidoreductase implicated in plant cell apoptosis (11), and that apoptosis in plants may also proceed through a ROS-directed pathway (11), adds further interest to this model.

Though observations by us and others are consistent with this model, they raise several unanswered questions. For example, we do not yet know which of the PIGS, are primarily responsible for the induction of ROS. We suspect that their combination, rather than any single one, is necessary for ROS generation. This conjecture is supported by preliminary experiments which demonstrate that PIG3 alone does not induce apoptosis when overexpressed. Though we have concentrated on the most highly induced PIGs, the SAGE analysis revealed at least 26 other genes which were induced by p53 to significant but lower levels than p21 and PIG1–PIG13. Some of these genes may play a role in redox regulation.

It is also not known why some cells enter into apoptosis following p53 expression while others undergo a prolonged growth arrest (4). The possibility that PIGs are only induced in the former has been excluded by examination of PIG expression in such lines; most PIGs were induced by p53 in each of ten CRC lines tested, regardless of whether the cells underwent apoptosis or growth arrest. A more likely possibility is that different cells have different capacities to cope with generators of oxidative stress and that cells with a low capacity succumb to apoptosis. This possibility is supported by numerous studies which show that the response to ROS varies significantly with cell type and growth conditions (13). Hopefully, the experiments and genes reported here will open a new window into the p53 apoptotic process that will facilitate inquiry into these issues.

References

1. Waldman, T., Kinzler, K. W. & Vogelstein, B. p21 is necessary for the p53-mediated G1 arrest in human cancer cells. Cancer Res. 55, 5187–5190 (1995).
2. Oren, M. Relationship of p53 to the control of apoptotic cell death. Semin. Cancer Biol. 5, 221–227 (1994).
3. Velculescu, V. E., Zhang, L., Vogelstein, B. & Kinzler, K. W. Serial Analysis Of Gene Expression. Science 270, 484–487 (1995).
4. Polyak, K., Waldman, T., He, T.-C., Kinzler, K. W. & Vogelstein, B. Genetic determinants of p53 induced apoptosis and growth arrest. Genes & Dev. 10, 1945–1952 (1996).
5. Levine, A. J. p53, the cellular gatekeeper for growth and division. Cell 88, 323–331 (1997).
6. Lehar, S. M., et al. Identification and cloning of Ei24, a gene induced by p53 in etoposide-treated cells. Oncogene 12, 1181–1187 (1996).
7. Hayward, D. C., et al. The sluggish-A gene of *Drosophila melanogaster* is expressed in the nervous system and encodes proline oxidase, a mitochondrial enzyme involved in glutamate biosynthesis. Proc. Natl. Acad. Sci. U.S.A. 90, 2979–2983 (1993).
8. Russo, T., et al. A p53-independent pathway for activation of WAF1/CIP1 expression following oxidative stress. J. Biol. Chem. 270, 29386–29391 (1995).
9. Rienhoff, H. Y., Jr., Huang, J. H., Li, X. X. & Liao, W. S. Molecular and cellular biology of serum amyloid A. Mol. Biol. Med. 7, 287–298 (1990).
10. Yamaoka, A., Kuwabara, I., Frigeri, I. G. & Liu, F. T. A human lectin, galectin-3 (epsilon bp/Mac-2) stimulates superoxide production by neutrophils. J. Immunol. 154, 3479–3487 (1995).
11. Greenberg, J. T. Programmed cell death: A way of life for plants. Proc. Natl. Acad. Sci. U.S.A. 93, 12094–12097 (1996).
12. Rao, P. V., Krishna, C. M. & Zigler, J. S., Jr. Identification and characterization of the enzymatic activity of zeta-crystallin from guinea PIG lens. A novel NADPH:quinone oxidoreductase. J. Biol. Chem. 267, 96–102 (1992).
13. Kroemer, G., Zamzami, N. & Susin, S. A. Mitochondrial control of apoptosis. Immun. Today 18, 45–51 (1997).
14. Zamzami, N., et al. Reduction in mitochondrial potential constitutes an early irreversible step of programmed lymphocyte death in vivo. 3. Exp. Med. 181, 1661–1672 (1995).
15. Petit, P. X., et al. Alterations in mitochondrial structure and function are early events of dexamethasone-induced thymocyte apoptosis. J. Cell. Biol. 130, 157–167 (1995).
16. Tamm, I. & Sehgal, P. B. Halobenzimidazole ribosides and RNA synthesis of cells and viruses. Adv. Virus Res. 22, 187–258 (1978).
17. Orrenius, S., Nobel, C. S. I., van den Dobbelsteen, D. J., Burkitt, M. J. & Slater, A. F. G. Dithiocarbamates and the redox regulation of cell death. Biochem. Soc. Transact. 24, 1032–1038 (1996).
18. Holland, P. C., Clark, M. G., Bloxham, D. P. &Lardy, H. A. Mechanism of action of the hypoglycemic agent diphenyleneiodonium. J. Biol. Chem. 248, 6050–6056 (1973).
19. Korsmeyer, S. J. Regulators of cell death. Trends Gen. 11, 101–105.
20. Susin, S. A., et al. Bcl-2 inhibits the mitochondrial release of an apoptogenic protease. J. Exp. Med. 184, 1331–1341 (1996).
21. Yang, J., et al. Prevention of apoptosis by Bcl-2: release of cytochrome c from mitochondria blocked. Science 275, 1129–1132 (1997).

22. KMuck, R. M., Bossy-Wetzel, E., Green, D. R. & Newmeyer, D. D. The release of cytochrome c from mitochondria: a primary site for Bcl-2 regulation of apoptosis. Science 275, 1132–1136 (1997).
23. Borek, C. Radiation and chemically induced transformation: free radicals, antioxidants and cancer. Br. J. Cancer Suppl. 8, 74–86 (1987).
24. Vayssiere, J. L., Petit, P. X., Risler, Y. & Mignotte, B. Commitment to apoptosis is associated with changes in mitochondrial biogenesis and activity in cell lines conditionally immortalized with simian virus 40. Proc. Natl. Acad. Sci. U. S. A. 91, 11752–11756 (1994).
25. Johnson, T. M., Yu, Z.-X., Ferrans, V. J., Lowenstein, R. A. & Finkel, T. Reactive oxygen species are downstream mediators of p53-dependent apoptosis. Proc. Natl. Acad. Sci. U. S. A. 93, 11848–11852 (1996).
26. El-Deiry, W. S., Tokino, T., Velculescu, V. E., Levy, D. B., Parsons, R., Trent, J. M., Lin, D., Mercer, W. E., Kinzler, K. W. & Vogelstein, B. WAF1, a potential mediator of p53 tumor supression. Cell 75, 817–825 (1993).
27. Velculescu, V. E., et al. Characterization of the yeast transcriptome. Cell 88 (1997).
28. El-Deiry, W. S., Kern, S. E., Pietenpol, J. A., Kinzer, K. W. & Vogelstein, B. Definition of a consensus binding site for p53. Nature Gen. 1, 45–49 (1992).
29. Faulkner, K. & Fridovich, I. Lurinol and lucigenin as detectors for $O_2$-.Free Rad. Biol.&Med. 15, 447–451 (1993).

TABLE 1[1]

| SEQ ID NO: | SAGE TAG | ACCESSION | DESCRIPTION |
| --- | --- | --- | --- |
| 4 | CCCGCCTCTT | D38112 | mitochondrial 16S rRNA |
| 4 | CCCGCCTCTT | T10098 | seq816 human cDNA clone b4HB3MA-COT8-HAP-Ft |
| 4 | CCCGCCTCTT | T10208 | seq907 human cDNA clone b4HB3MA-COT8-HAP-Ft |
| 4 | CCCGCCTCTT | T26521 | AB291H2F human cDNA clone LLAB291H2 3'. |
| 4 | CCCGCCTCTT | W27281 | 28g3 human retina cDNA randomly primed sublibrary |
| 4 | CCCGCCTCTT | T17062 | NIB250 human cDNA 3'end similar to human mitochondrial mRNA |
| 5 | AATCTGCGCC | M13755 | human interferon-induced 17-kDa/15-kDa protein mRNA* |
| 5 | AATCTGCGCC | M21786 | human interferon-induced 15-Kd protein (ISG) gene* |
| 6 | GTGACCACGG | K03432 | 18S rRNA |
| 7 | TTTCCTCTCA | X57348 | human mRNA (clone 9112). |
| 8 | TGCCTGCACC | X61683 | human gene for cystatin C exon 3 |
| 8 | TGCCTGCACC | X05607 | human mRNA for cysteine proteinase inhibitor precursor |
| 9 | TCACCCACAC | R01174 | ye77b03.s1 human cDNA clone 123725 3' |
| 9 | TCACCCACAC | N95827 | zb66e05.s1 human cDNA clone 308576 3' |
| 10 | TAAACCTGCT | U06643 | PIG1, human keratinocyte lectin 14 (HKL-14) mRNA* |
| 10 | TAAACCTGCT | L07769 | PIG1, human galectin-7 mRNA, complete CDS.* |
| 11 | CCCAAGCTAG | X54079 | human mRNA for heat shock protein HSP27 |
| 12 | AGCCCGCCGC | AF001294 | human IPL (IPL) mRNA |
| 12 | AGCCCGCCGC | N29541 | yw89f12.s1 human cDNA clone 259439 3' |
| 13 | GACATCAAGT | Y00503 | human mRNA for keratin 19. |
| 13 | GACATCAAGT | J03607 | human 40-kDa keratin intermediate filament precursor |
| 14 | TGTCCTGGTT | U03106 | human wild-type p53 activated fragment-1 (WAF1)* |
| 14 | TGTCCTGGTT | U09579 | human melanoma differentiation associated (mda-6)* |
| 14 | TGTCCTGGTT | L26165 | human DNA synthesis inhibitor mRNA, complete CDS.* |
| 14 | TGTCCTGGTT | L25610 | human cyclin-dependent kinase inhibitor mRNA* |
| 15 | AGCTCACTCC | AF010314 | PIG10, homologous to none* |
| 16 | AGGCTGTCCA | AF010315 | PIG11, homologous to none* |
| 17 | TGAGTCCCTG | AF010316 | PIG12, microsomal GST homolog* |
| 18 | CCCTCCTCCG | F19653 | PIG2, human EST sequence (011-X4-27) from skeletal muscle* |
| 18 | CCCTCCTCCG | Z49878 | PIG2, Guanidinoacetate N-methyltransferase* |
| 19 | GAGGCCAACA | AF010309 | PIG3, quinone oxidoreductase homologue |
| 19 | GAGGCCAACA | H42923 | yo10e11.s1 human cDNA clone 177548 3'. |
| 19 | GAGGCCAACA | W07320 | za94c09.r1 Soares fetal lung NbHL19W human |
| 20 | TGGGGCCGCA | U33271 | PIG5, human normal keratinocyte mRNA, clone B4, partial* |
| 21 | TCCTTGGACC | AF010311 | PIG36, homologous to Drosophila PUT1, partial* |
| 22 | CTGGGCCTGA | AF010312 | PIG7* |
| 23 | AGCTGGTTTCC | AF010313 | PIG8, human homolog of mouse EI24* |

TABLE 1¹-continued

| SEQ ID NO: | SAGE TAG | ACCESSION | DESCRIPTION |
|---|---|---|---|
| 24 | GAGGTGCCGG | J00277 J00206 J00276 K00954 | human (genomic clones lambda-[SK2-T2, HS578T]; cDNA clones RS-[3, 4, 6]) c-Ha-ras1 proto-oncogene, complete coding sequence |
| 24 | GAGGTGCCGG | W25059 | zb67e08.r1 Soares fetal lung NbHL19W human |
| 25 | ACAACGTCCA | T16546 | NIB1466 human cDNA 3'end |
| 25 | ACAACGTCCA | D85815 | human DNA for rhoHP1 |
| 26 | GTGCGGAGGA | X56653 | PIG4, human SAA2 alpha gene, exon 3 and exon 4* |
| 26 | GTGCGGAGGA | X51439 | PIG4, human mRNA for serum amyloid A (SAA) protein partial* |
| 26 | GTGCGGAGGA | X51441 | PIG4, human mRNA for serum amyloid A (SAA) protein partial* |
| 26 | GTGCGGAGGA | X51442 | PIG4, human mRNA for serum amyloid A (SAA) protein partial* |
| 26 | GTGCGGAGGA | X51445 | PIG4, human mRNA for serum amyloid A (SAA) protein partial* |
| 26 | GTGCGGAGGA | M23698 | PIG4, human serum amyloid A1 (SAA1) mRNA, complete* |
| 26 | GTGCGGAGGA | M23699 | PIG4, human serum amyloid A2-alpha (SAA2) mRNA* |
| 26 | GTGCGGAGGA | M26152 | PIG4, human serum amyloid A (SAA) mRNA, complete* |
| 26 | GTGCGGAGGA | M10906 | PIG4, human serum amyloid A (SAA) mRNA* |
| 26 | GTGCGGAGGA | H45773 | PIG4, yp23c09.r1 human cDNA clone 188272 5' simil* |
| 26 | GTGCGGAGGA | T28677 | PIG4, E5T51616 human cDNA 5' end similar to serum* |
| 27 | CGTCCCGGAG | U33822 | PIG9, human tax1-binding protein TXBP181 mRNA, complete* |
| 27 | CGTCCCGGAG | D52048 | PIG9, human fetal brain cDNA 5'-end GEN-064D09* |
| 28 | GTGCTCATTC | AB000584 | human mRNA for TGF-beta superfamily protein |
| 29 | GCTGACTCAG | M99425 | human thrombospondin mRNA, 3' end. |
| 30 | AGATGCTGCA | | PIG13 |
| 31 | CTCAGACAGT | AA046881 | EST homologous to 40S ribosomal protein |
| 32 | TCCGGCCGCG | | NO MATCH |
| 33 | AGCCACTGCA | | Alu repeat |
| 34 | GCTTTTAAGG | L06498 | human ribosomal protein S20 (RPS20) mRNA |
| 35 | GGGCCAATAA | D29121 | human keratinocyte cDNA, clone 142 |
| 35 | GGGCCAATAA | AA178918 | human cDNA clone 612020 |
| 36 | AAGGGCTCTT | M20560 | human lipocortin-III mRNA |
| 36 | AAGGGCTCTT | M63310 | human 1,2-cyclic-inositol-phosphate phosphodiesterase (ANX3) mRNA |

¹Gene assignments were based on the following list of GenBank sequences (GenBank Release 94). In each case, tentative assignments were based on the identification of a 10 bp SAGE tag adjacent to a NlaIII site. The final assignment was further refined by using an 11 bp SAGE tag and elimination of non 3' end NlaIII sites and genomic sequences. In some cases, the assignment was confirmed by Northern blot analysis as indicated by the asterisk following the description. In other cases, a single assignment could not be made, and more than one gene is listed.

TABLE 2²

| SEQ ID NO: | SAGE TAG | ACCESSION NUMBER | DESCRIPTION |
|---|---|---|---|
| 37 | GTAAGTGTAC | J01415 | 12S rRNA |
| 38 | TGTACCTGTA | K00558 | human alpha-tubulin mRNA |
| 39 | AACGACCTCG | V00599 | human mRNA fragment encoding beta-tubulin |
| 40 | AGTTTGTTAG | M33011 | human carcinoma-associated antigen GA733-2 mRNA |
| 41 | GACTCGCCCA | M98326 | human P1-Cdc46 mRNA |
| 42 | GGGCCAATAA | D29121 | human keratinocyte cDNA, clone 142 |
| 42 | GGGCCAATAA | AA178918 | human cDNA clone 612020 |

TABLE 2²-continued

| SEQ ID NO: | SAGE TAG | ACCESSION NUMBER | DESCRIPTION |
|---|---|---|---|
| 43 | GGGTTTTTAT | L28809 | human dbpB-like protein mRNA |
| 44 | AGAAATACCA | AA455253 | human cDNA clone 814816 3' |
| 45 | TACCATCAAT | J02642 | human glyceraldehyde 3-phosphate dehydrogenase mRNA |
| 46 | GGATTGTCTG | M34081 | human small nuclear ribonucleoprotein particle SmB mRNA |
| 47 | TACTAGTCCT | X15183 | human mRNA for 90-kDa heat-shock protein |
| 48 | AATATTGAGA | U62962 | human Int-6 mRNA, complete CDs |
| 49 | GAGGGAGTTT | U14968 | human ribosomal protein L27a mRNA |
| 50 | AAGGGCGCGG | M20560 | human lipocortin-III mRNA |
| 50 | AAGGGCGCGG | M63310 | human 1,2-cyclic-inositol-phosphate phosphodiesterase (ANX3) mRNA |
| 51 | TTCACAAAGG | X61970 | human mRNA for macropain subunit zeta |
| 52 | CTGCACTTAC | D28480 | human mRNA for hMCM2 |
| 53 | GATCCCAACT | V00594 | human mRNA for metallothionein from cadmium-treated cells |
| 54 | GGGAAGCAGA | X77770 | mitochondrial mRNA |
| 55 | GCTTTCTCAC | K00365 | human mitochondrial Ser-tRNA |
| 56 | TTCATTATAA | M26708 | human prothymosin alpha mRNA |
| 57 | TAAGGAGCTG | X77770 | human RPS26 mRNA |
| 58 | TGAGGGAATA | M10036 | human triosephosphate isomerase mRNA |
| 59 | GGGATGGCAG | M98326 | human transfer valyl-tRNA synthetase mRNA |
| 60 | TCTTCTCTG | | NO MATCH |
| 61 | GCACCTTATT | | NO MATCH |
| 62 | ACTTTAAACT | | NO MATCH |
| 63 | CCATTCCACT | | NO MATCH |
| 64 | TCAAATGCAT | M16342 | human small nuclear ribonucleoprotein (hnRNP) C protein mRNA |
| 65 | GAAAAATGGT | X61156 | human mRNA for laminin-binding protein |
| 66 | ACTAACACCC | U18810 | human PACAP type-e/VIP type-2 receptor mRNA |
| 67 | TTGGGGTTTC | M12937 | human ferritin heavy subunit mRNA |

²Gene assignments were based on the following list of GenBank sequences (GenBank Release 94). In each case, tentative assignments were based on the identification of a 10 bp SAGE tag adjacent to a NlaIII site. The final assignment was further refined by using an 11 bp SAGE tag and elimination of non 3' end NlaIII sites and genomic sequences.

What is claimed is:

1. A method of screening for cancer or p53 status in a sample suspected of being neoplastic, comprising the steps of:

comparing the level of transcription of an RNA transcript in a first sample of a first tissue to the level of transcription of the transcript in a second sample of a second tissue, wherein the first tissue is a human tissue suspected of being neoplastic and the second tissue is a normal human tissue, wherein the first and second tissue are of the same tissue type, and wherein the transcript is identified by a nucleic acid consisting of a tag set forth as SEQ ID NO:19, and wherein the tag is located 3' of the 3'-most site for a NlaIII restriction endonuclease in a cDNA reverse transcribed from the transcript;

categorizing the first sample as likely to be neoplastic or likely to have a mutant p53 when transcription is found to be the same or lower in the first sample than in the second sample.

2. A DNA construct for screening drugs as anti-neoplastic agents comprising:

a reporter gene under the control of a PIG-3 promoter, wherein the reporter gene is 3' and covalently linked to the PIG-3 promoter, wherein the PIG-3 promoter comprises the sequence CAGCTTGCCCACCCATGCTC (SEQ ID NO:1).

3. A method of screening for cancer or p53 status in a human sample suspected of being neoplastic, comprising the steps of:

treating cells of the sample with a DNA-damaging agent;

comparing the level of transcription of an RNA transcript in cells of the sample to the level of transcription of the transcript in cells of the sample which are not subject to said treating, wherein the transcript is identified by a nucleic acid consisting of a tag set forth as SEQ ID NO:19, and wherein the tag is located 3' of the 3'-most site for a NlaIII restriction endonuclease in a cDNA reverse transcribed from the transcript;

categorizing the sample as likely to be neoplastic or likely to have a mutant p53 when transcription is found to be the same or lower in the treated cells than in the untreated cells.

4. The method of claim 1 wherein the first and second samples are treated with a DNA-damaging agent prior to said step of comparing.

* * * * *